United States Patent
Ozawa et al.

(10) Patent No.: US 6,858,004 B1
(45) Date of Patent: Feb. 22, 2005

(54) ELECTRONIC ENDOSCOPE SYSTEM INCLUDING A PLURALITY OF VIDEO-PROCESSORS

(75) Inventors: Ryo Ozawa, Tokyo (JP); Makoto Koike, Saitama (JP); Hiroyuki Kobayashi, Tokyo (JP); Kohei Iketani, Saitama (JP); Hideo Sugimoto, Tokyo (JP)

(73) Assignee: PENTAX Corporation, Tokyo (JP)

( * ) Notice: Subject to any disclaimer, the term of this patent is extended or adjusted under 35 U.S.C. 154(b) by 573 days.

(21) Appl. No.: 09/709,709

(22) Filed: Nov. 13, 2000

(30) Foreign Application Priority Data

Nov. 12, 1999  (JP) .......................................... P11-322813
Jun. 27, 2000  (JP) ..................................... P2000-192258

(51) Int. Cl.[7] .............................. A61B 1/00; H04N 9/47

(52) U.S. Cl. ........................................ 600/118; 348/65

(58) Field of Search ................................ 600/118, 101, 600/103, 920, 169, 102, 104; 348/65, 705, 72, 75, 45, 47, 48–52

(56) References Cited

U.S. PATENT DOCUMENTS

| | | | | |
|---|---|---|---|---|
| 4,394,745 A | * | 7/1983 | Menezes et al. | 386/54 |
| 4,667,229 A | * | 5/1987 | Cooper et al. | 348/71 |
| 4,746,975 A | * | 5/1988 | Ogiu | 348/76 |
| 5,111,306 A | * | 5/1992 | Kanno et al. | 358/403 |
| 5,143,054 A | * | 9/1992 | Adair | 600/104 |
| 5,278,642 A | * | 1/1994 | Danna et al. | 348/70 |
| 5,622,528 A | * | 4/1997 | Hamano et al. | 600/118 |
| 5,902,230 A | * | 5/1999 | Takahashi et al. | 600/109 |
| 6,246,432 B1 | * | 6/2001 | Takami et al. | 348/65 |

* cited by examiner

*Primary Examiner*—Daniel Robinson
(74) *Attorney, Agent, or Firm*—Greenblum & Bernstein, P.L.C.

(57) ABSTRACT

An electronic endoscope system has a plurality of video-processors, a plurality of video-scopes, a selector, a monitor and an input device. The plurality of video-processors, the monitor and the input device are connected to the selector. Each of the plurality of video-processors processes image signals from the corresponding video-scope to obtain and output video signals to the selector. The selector selects one of the plurality of video-processors and feeds video signals from a selected video-processor to the monitor. The input device operates the selected video-processor.

30 Claims, 23 Drawing Sheets

FIG. 5

| | JK FLIP-FLOP | | | | MULTIPLEXER | | 4 SWITCHES |
|---|---|---|---|---|---|---|---|
| | CLEAR (KPS1) | PRESET (KPS2) | CLK | QS | SELECTED SIGNAL | SS | SELECTED VIDEO-PROCESSOR |
| 1 INITIAL STATE (NO POWER) | L | L | H | H | KPS2' | H | FIRST VIDEO-PROCESSOR |
| 2 FIRST VIDEO-PROCESSOR POWER ON | H | L | H | H | KPS2' | H | FIRST VIDEO-PROCESSOR |
| 3 SECOND VIDEO-PROCESSOR POWER ON | H | H | H | H | KPS2' | L | SECOND VIDEO-PROCESSOR |
| 4 FIRST PUSHING OF PUSH SWITCH | H | H | ⤓ | L | KPS1 | H | FIRST VIDEO-PROCESSOR |
| 5 SECOND PUSHING OF PUSH SWITCH | H | H | ⤓ | H | KPS2' | L | SECOND VIDEO-PROCESSOR |

T1

L···LOW LEVEL  H···HIGH LEVEL
⤓···TRANSITION FROM HI TO LOW

FIG. 6

| | | JK FLIP-FLOP | | | MULTIPLEXER | | 4 SWITCHES |
|---|---|---|---|---|---|---|---|
| | | CLEAR (KPS1) | PRESET (KPS2) | CLK | QS | SELECTED SIGNAL | SS | SELECTED VIDEO-PROCESSOR |
| 1 | INITIAL STATE (NO POWER) | L | L | H | H | KPS2' | H | FIRST VIDEO-PROCESSOR |
| 2 | SECOND VIDEO-PROCESSOR POWER ON | L | H | H | L | KPS1 | L | SECOND VIDEO-PROCESSOR |
| 3 | FIRST VIDEO-PROCESSOR POWER ON | H | H | H | L | KPS1 | H | FIRST VIDEO-PROCESSOR |
| 4 | FIRST PUSHING OF PUSH SWITCH | H | H | ↴ | H | KPS2' | L | SECOND VIDEO-PROCESSOR |
| 5 | SECOND PUSHING OF PUSH SWITCH | H | H | ↴ | L | KPS1 | H | FIRST VIDEO-PROCESSOR |

T2

↴ ··· TRANSITION FROM HI TO LOW  
L ··· LOW LEVEL  
H ··· HIGH LEVEL

FIG. 8

| | SS | KPS1 | KPS2 | NP0 | NP1 | NP2 | NP3 | NP4 | FIRST I.L. | SECOND I.L. |
|---|---|---|---|---|---|---|---|---|---|---|
| 1 | INITIAL STATE (NO POWER) | H | L | L | H | H | H | L | H | × | × |
| 2 | FIRST VIDEO-PROCESSOR POWER ON | H | H | L | H | L | H | H | L | ○ | × |
| 3 | SECOND VIDEO-PROCESSOR POWER ON | L | H | H | L | H | H | L | H | × | ○ |
| 4 | FIRST PUSHING OF PUSH SWITCH | H | H | H | H | L | L | H | L | ○ | × |
| 5 | SECOND PUSHING OF PUSH SWITCH | L | H | H | L | H | H | L | H | × | ○ |

T3

○···TURN ON
×···TURN OFF

L···LOW
H···HIGH

| | | SS | KPS1 | KPS2 | NP0 | NP1 | NP2 | NP3 | NP4 | FIRST I.L. | SECOND I.L. |
|---|---|---|---|---|---|---|---|---|---|---|---|
| 1 | INITIAL STATE (NO POWER) | H | L | L | H | H | H | L | H | × | × |
| 2 | SECOND VIDEO-PROCESSOR POWER ON | L | L | H | L | H | H | L | H | × | ○ |
| 3 | FIRST VIDEO-PROCESSOR POWER ON | H | H | H | H | L | L | H | L | ○ | × |
| 4 | FIRST PUSHING OF PUSH SWITCH | L | H | H | L | H | H | L | H | × | ○ |
| 5 | SECOND PUSHING OF PUSH SWITCH | H | H | H | H | L | L | H | L | ○ | × |

○···TURN ON
×···TURN OFF

L···LOW
H···HIGH

| SW1 | SW2 | SW3 | SW4 | TYPES OF VIDEO-PROCESSORS |
|---|---|---|---|---|
| OPEN | OPEN | — | — | VPFA |
| CLOSE | OPEN | — | — | VPFB |
| OPEN | CLOSE | — | — | VPFC |
| CLOSE | CLOSE | — | — | VPFD |
| — | — | OPEN | OPEN | VPSA |
| — | — | CLOSE | OPEN | VPSB |
| — | — | OPEN | CLOSE | VPSC |
| — | — | CLOSE | CLOSE | VPSD |

| INPUT SIGNALS | | | | | INDICATING SIGNAL (KIS) |
|---|---|---|---|---|---|
| TI0 | TI1 | TI2 | TI3 | TI4 | |
| H | H | H | — | — | E1 |
| H | L | H | — | — | E2 |
| H | H | L | — | — | E3 |
| H | L | L | — | — | E4 |
| L | — | — | H | H | E5 |
| L | — | — | L | H | E6 |
| L | — | — | H | L | E7 |
| L | — | — | L | L | E8 |

| INDICATING SIGNAL | LED | ILLUMINATED SIGN |
|---|---|---|
| E1 | LED1 | VPFA |
| E2 | LED2 | VPFB |
| E3 | LED3 | VPFC |
| E4 | LED4 | VPFD |
| E5 | LED5 | VPSA |
| E6 | LED6 | VPSB |
| E7 | LED7 | VPSC |
| E8 | LED8 | VPSD |

ELECTRONIC ENDOSCOPE SYSTEM INCLUDING A PLURALITY OF VIDEO-PROCESSORS

BACKGROUND OF THE INVENTION

1. Field of the Invention

The present invention relates to an electronic endoscope, which includes a video-scope having an image sensor for photographing an observed area of internal organs and a video-processor for processing image signals read from the image sensor, to which the video-scope is connected. In particular, the present invention relates to an electronic endoscope system using a plurality of video-processors.

2. Description of the Related Art

In the electronic endoscope system, a video-scope has an image sensor and a light guide (fiber-optic bundle) for transmitting light and the video-scope is detachably connected to a video-processor. When an inspection or an operation is executed, the video-scope is inserted into the body cavity. Light, radiating from a light source provided in the video-processor, passes through the light guide and radiates from the distal end of the video-scope, thus the observed area is illuminated. An object image is formed on the image sensor and the image-pixel signals corresponding to the object image are read from the image sensor. The video-processor processes the image-pixel signals so that video signals are generated and fed to a TV monitor, which is connected to the video-processor. Thus, the object image is displayed on the monitor. Further, an input device for operating the video-processor, such as a keyboard, a recorder for recording the object image and a computer system for filing object images are provided in the electronic endoscope system. The input device, the recorder and the computer system are connected to the video-processor. The video-scope varies with the observed area in the body cavity. For example, the type of video-scope for observing bronchial tubes is different from that for observing a large intestine. When the examination or operation is performed, a video-scope appropriate for the area to be observed is selected from among the plurality of the video-scopes and connected to the video-processor.

Recently, to observe different positions during one examination or operation, or to perform a examination of many people consecutively, a plurality of video-processors and video-scopes are utilized in the electronic endoscope system. In this case, a plurality of monitors and keyboards are prepared to coincide with the number of video-processors.

However, since a plurality of video-processors, monitors and keyboards are needed, the cost of the electronic endoscope system is high and a large space for setting up the electronic endoscope system should is needed. Further, assembly of the electronic endoscope system becomes complicated, the operator must operate various apparatus, each of which is different in operation. In consequence, a problem may occur whereby the efficiency of the diagnosis decreases.

SUMMARY OF THE INVENTION

Therefore, an object of the present invention is to provide an electronic endoscope system, which needs only a small setup space, reduces costs and lifts a diagnostic efficiency.

An electronic endoscope system according to the present invention has a plurality of video-scopes, a plurality of video-processors, a selector, a monitor and an input device. Each of the plurality of video-scopes has an image sensor on which an object image is formed and is detachably connected to the corresponding video-processor among the plurality of the video-processors. Each video-processor processes image signals read from the corresponding image sensor to obtain and output video signals. The plurality of video-processors is connected to the selector respectively and the selector selects one of the plurality of video-processors and outputs video signals fed from a selected video-processor from the plurality of video-processors. The monitor is connected to the selector and displays the object image on the basis of the video signals fed via the selector, from the selected video-processor. The input device for operating the selected video-processor is connected to the plurality of video-processors via the selector. An operator utilizes the input device to operate the selected video-processor. The plurality of displays and input devices are reduced to one by using the selector and the operator utilize only one input device. Therefore, space necessary for setting up the electronic endoscope system becomes small, cost is suppressed and the efficiency of the diagnosis is increased.

When one of the plurality of video-processor is turned ON, preferably, the selector detects the active video-processor from among the plurality of video-processors. The selector then outputs video signals fed from the active video-processor to the monitor. On the other hand, when at least two video-processors of the plurality of video-processors are turned ON, preferably, the selector detects a last activated video-processor, which is activated last from among the plurality of video-processors. The selector then outputs the video signals fed from the last activated video-processor to the monitor.

For detecting of the operating state of the plurality of video-processors, preferably, the selector receives a plurality of electric power signals fed from the plurality of video-processors and represent an operating state of each of the video-processors respectively, via a plurality of input device cables. The plurality of input device cables are connected between the video-processors and the selector respectively so as to transmit an input device operating signal, output from the input device, to the selected video-processor. In this case, the selector detects the active video-processor or the last activated video-processor in accordance with the plurality of electric power signals. The selector outputs video signals fed from one of the active video-processor and the last activated video-processor to the monitor. As the plurality of electric power signals are fed to the input device cables, the selector detects the operating state of the plurality of the video-processors without using separate cables for the plurality of electric power signals.

Preferably, the selector has a manually operated selecting switch for selecting one of the plurality of video-processors such that operator may select one of the plurality of video-processors if needed. The selector outputs the video signals fed from the selected video-processor, which is selected by the selecting switch.

Preferably, the selector has a reset signal generator that feeds a reset signal to the selected video-processor among the plurality of video-processors such that the selected video-processor is reset. The selected video-processor returns to a processor initial state.

Preferably, the plurality of video-processors is composed of a first video-processor and a second video-processor, the input device is a keyboard and the selector has a video signal switch circuit and a selecting controller. The video signal switch circuit, to which first video signals fed from the first video-processor and second video signals fed from the second video-processor are input, selectively outputs the first video signals or the second video signals to the monitor. The selecting controller selects the first or second video-processors and controls the video signal switch circuit such that either the first or second video signals, fed from the selected video-processor, is fed to the monitor. Further, preferably, the selector has a keyboard switch circuit, to which a keyboard operating signal generated by operating the keyboard is input. The keyboard switch circuit selectively feeds the keyboard operating signal to either the first video-processor or the second video-processor. The selecting controller controls the keyboard switch circuit such that the keyboard operating signal is fed to the selected video-processor.

Preferably, a first electric power signal fed from the first video-processor and a second electric power signal fed from the second video-processor, which represent the active state of the first and second video-processors respectively, are input to the selector. In this case, the selecting controller detects which video-processor is turned ON from among the first and second video-processors, on the basis of the first and second electric power signals. The selecting controller then controls the video signal switch circuit such that either the first video signals and or second video signal, output from the first or second video-processor, whichever is turned ON, is fed to the monitor.

On the other hand, when the first and second video-processors are turned ON, preferably, the selecting controller detects which video-processor is turned ON last among the first and second video-processors on the basis of the first and second electric power signals. The selecting controller then controls the video signal switch circuit such that either the first video signals or the second video signal, output from the first or second video-processor, whichever is turned ON last, is fed to the monitor.

To detect of the active state of the first and second video-processors, preferably, the first and second electric power signals are fed to the selector via first and second keyboard cables, respectively. The first and second keyboard cables are connected between the selector and the first and second video-processors respectively to transmit a keyboard operating signal generated by operating the keyboard to one of the first and second video-processors.

Preferably, the selector has a manually operated selecting switch for alternately selecting the first video-processor and the second video-processor. In this case, the selecting controller receives an operating signal generated by operating the selecting switch, and controls the video signal switch circuit in accordance with the operating signal, such that either the first or second video signal, fed from the first or second video-processor selected by the selecting switch, is fed to the monitor.

For preferable construction of the selecting controller, the selecting controller has a JK flip-flop with clock, clear and preset inputs, an inverter and a multiplexer. The first electric power signal and the second electric power signal are input to the clear and preset inputs respectively and the operating signal is input to the clock input. The JK flip-flop outputs a state signal in accordance with levels of the first and second electric power signals and an input of the operating signal. The inverter inverts a level of the second electric power signal to generate an inverted second electric power signal. The state signal, the first electric power signal and the inverted second electric power signal are input to the multiplexer. The multiplexer selectively outputs either the first electric power signal or the inverted second electric power signal to the video signal switch circuit as a selecting signal, in accordance with a level of the state signal. The video signal switch circuit is switched in accordance with a level of the selecting signal.

Preferably, the selector has a reset signal generator. The reset signal generator feeds a reset signal to the selected video-processor of the first and second video-processors such that the selected video-processor is reset, when the level of the selecting signal changes, Preferably, the electronic endoscope system has a computer connected to the selector. A memory device for storing the object image and a display for the computer are connected to the computer. The selector selectively outputs the video signal fed from the selected video-processor to the computer.

According to another aspect of the present invention, a selector of the present invention, incorporated in an electronic endoscope system, which includes a plurality of video-processors and a monitor, has a video signal switch circuit and a selecting controller. The video signal switch circuit, which receives a plurality of video signals fed from the plurality of video-processors respectively, selectively outputs one of the plurality of video signals to the monitor. The selecting controller selects one of the plurality of video-processors and controls the video signal switch circuit such that video signals output from a selected video-processor are fed to the monitor.

Preferably, an input device for operating the selected video-processor is included in the electronic endoscope system, and connected to the selector, which includes an input device signal switch circuit. An input device operating signal, generated by operating the input device, is input to the input device signal switch circuit which selectively feeds the input device operating signal to one of the video-processors. The selecting controller controls the input device signal switch circuit such that the input device operating signal is fed to the selected video-processor.

According to another aspect of the present invention, an electronic endoscope system of the present invention has a plurality of video-scopes, a plurality of video-processors, a selector, a monitor, an input device and an indicator. Each of the plurality of video-scopes has an image sensor on which an object image is formed. The plurality of video-scopes is detachably connected to the plurality of video-processors respectively. Each video-processor processes image signals read from the corresponding image sensor to obtain and output video signals. The plurality of video-processors are connected to the selector respectively and the selector selects one of the plurality of video-processors and outputs video signals fed from the selected video-processor of the plurality of video-processors. The monitor is connected to the selector and displays the object image on the basis of the video signals fed from the selector. The input device for operating the selected video-processor is connected to the plurality of video-processors via the selector. An operator utilizes the input device to operate the selected video-processor. The indicator visually indicates the selected video-processor among the plurality of video-processors. The operator recognizes the selected video-processor visually by the indicator, so a mistake when using the input device is avoided.

Preferably, an indicator is provided at the selector such that the selected video-processor is indicated on the selector. For example, the indicator has indicating lamps, the number of which corresponds to the number of video-processors.

The indicator then illuminates one lamp, which corresponds to the selected video-processor.

Preferably, the indicator displays processor information representing the selected video-processor on the monitor. In this case, for example, the indicator has a superimposing circuit. The superimposing circuit superimposes character signal representing the selected video-processor into the video signals fed from the selected video-processor, such that the processor information is displayed at a predetermined position on the monitor.

Preferably, the input device is a keyboard. In this case, preferably, the indicator has a selected processor displayer provided at the keyboard and a processor detector provided in the selector. The selected processor displayer displays the selected video-processor. The processor detector detects the selected video-processor and feeds an indicating signal corresponding to the selected video-processor to the selected processor displayer. The indicator indicates the selected video-processor at the selected processor displayer in accordance with the indicating signal. Generally, the operating manner the keyboard varies with the color photographing process. As the selected video-processor is indicated at the keyboard, incorrect operation of the keyboard is avoided.

For example, the selected processor displayer has a plurality of luminance devices, the number of which corresponds to the number of the video-processors. In this case, the indicator illuminates one luminance device, corresponding to the selected video-processor, among the plurality of luminous devices. For example, the selected processor displayer has an LCD (Liquid Crystal Device) and the indicator displays the selected video-processor on the LCD.

The operation of a video-processor using a keyboard varies with the processor type. Accordingly, preferably, the selector has a processor type setting switch for registering different types of video-processors. The indicator then indicates which type of video-processor is selected in accordance with the position of the processor type setting switch.

Preferably, the plurality of the video-processors are composed of a first video-processor which corresponds to a R, G, B sequential method for a color photographing process and a second video-processor which corresponds to a color chip filter method for the color photographing process. In this case, the indicator indicates the type of the first video-processor or the type of the second video-processor, which is selected by the selector.

According to another aspect of the present invention, A selector of the present invention is incorporated in an electronic endoscope system which includes a plurality of video-processors, an input device and a monitor, and has a video signal circuit, a selecting controller, an input device signal switch circuit and an indicating processor. The video signal switch circuit, to which a plurality of video signals fed from the plurality of video-processors respectively are input, selectively outputs one of the plurality of video signals to the monitor. The selecting controller selects one of video-processors and controls the video signal switch circuit such that video signals fed from the selected video-processor are fed to the monitor. An input device operating signal, generated by operating the input device, is input to the input device signal switch circuit which selectively feeds the input device operating signal to one of the video-processors. The selecting controller controls the input device signal switch circuit such that the input device operating signal is fed to the selected video-processor. The indicating processor superimposes a character signal representing the selected video-processor into the video signals to display the identity of the selected video-processor on the monitor.

According to another aspect of the present invention, a selector and input device of the present invention are incorporated in an electronic endoscope system including a monitor and a plurality of video-processors, and has a video signal switch circuit, a selecting controller, an input device signal switch circuit, an input device indicator and a processor detector. The video signal switch circuit, provided in the selector, to which a plurality of video signals fed from the plurality of video-processors respectively are input, selectively outputs one of the plurality of video signals to the monitor. The selecting controller, provided in the selector, selects one of video-processors and controls the video signal switch circuit such that video signals output from the selected video-processor is fed to the monitor. The input device signal switch circuit is provided in the selector. An input device operating signal, generated by operating the input device, is input to the input device signal switch circuit which selectively feeds the input device operating signal to one of the video-processors. The selecting controller controls the input device signal switch circuit such that the input device operating signal is fed to the selected video-processor. The input device indicator is provided at the input device and has a selected processor displayer for displaying the selected video-processor. The processor detector, provided in the selector, detects the selected video-processor and feeds an indicating signal corresponding to said selected video-processor to said input device indicator. The input device indicator displays the selected video-processor at the selected processor displayer in accordance with the indicating signal.

According to another aspect of the present invention, a selector of the present invention is incorporated in an electronic endoscope system including a plurality of video-processors, input device and a monitor, and has a video signal circuit, a selecting controller, an input device signal switch circuit and an indicator. The video signal switch circuit, to which a plurality of video signals fed from the plurality of video-processors respectively are input, selectively outputs one of the plurality of video signals to the monitor. The selecting controller selects one of the video-processors and controls the switch circuit such that video signals output from the selected video-processor is fed to the monitor. An input device operating signal, generated by operating the input device, is input to the input device signal switch circuit which selectively feeds the input device operating signal to one of the video-processors. The selecting controller controls the input device signal switch circuit such that the input device operating signal is fed to the selected video-processor. The indicator visually indicates the selected video-processor on the selector.

BRIEF DESCRIPTION OF THE DRAWINGS

The present invention will be better understood from the description of the preferred embodiment of the invention set fourth below together with the accompanying drawings, in which:

FIG. 5 is a table indicating the relationship between a first and second electric power signal, an operating signal and a selecting signal in when a first video-processor is turned ON first.

FIG. 6 is a table indicating the relationship between a first and second electric power signal, an operating signal and a selecting signal when a second video-processor is turned ON first.

FIG. 8 is a table indicating the state of first and second indicator lamps when the first video-processor is turned ON first FIG. 9 is a table indicating the state of the first and second indicator lamps when the second video-processor is turned ON first.

FIG. 14 is a table indicating the setting positions of slide switches according to the type of first and second video-processors.

FIG. 16 is a table indicating the relationship between an indicating signal and the input signal level.

FIG. 18 is a table indicating the relationship between the indicating signal, illuminated LEDs and video-processor types.

DESCRIPTION OF THE PREFERRED EMBODIMENTS

Hereinafter, the preferred embodiment of the present invention is described with reference to the attached drawings.

Figure 1:
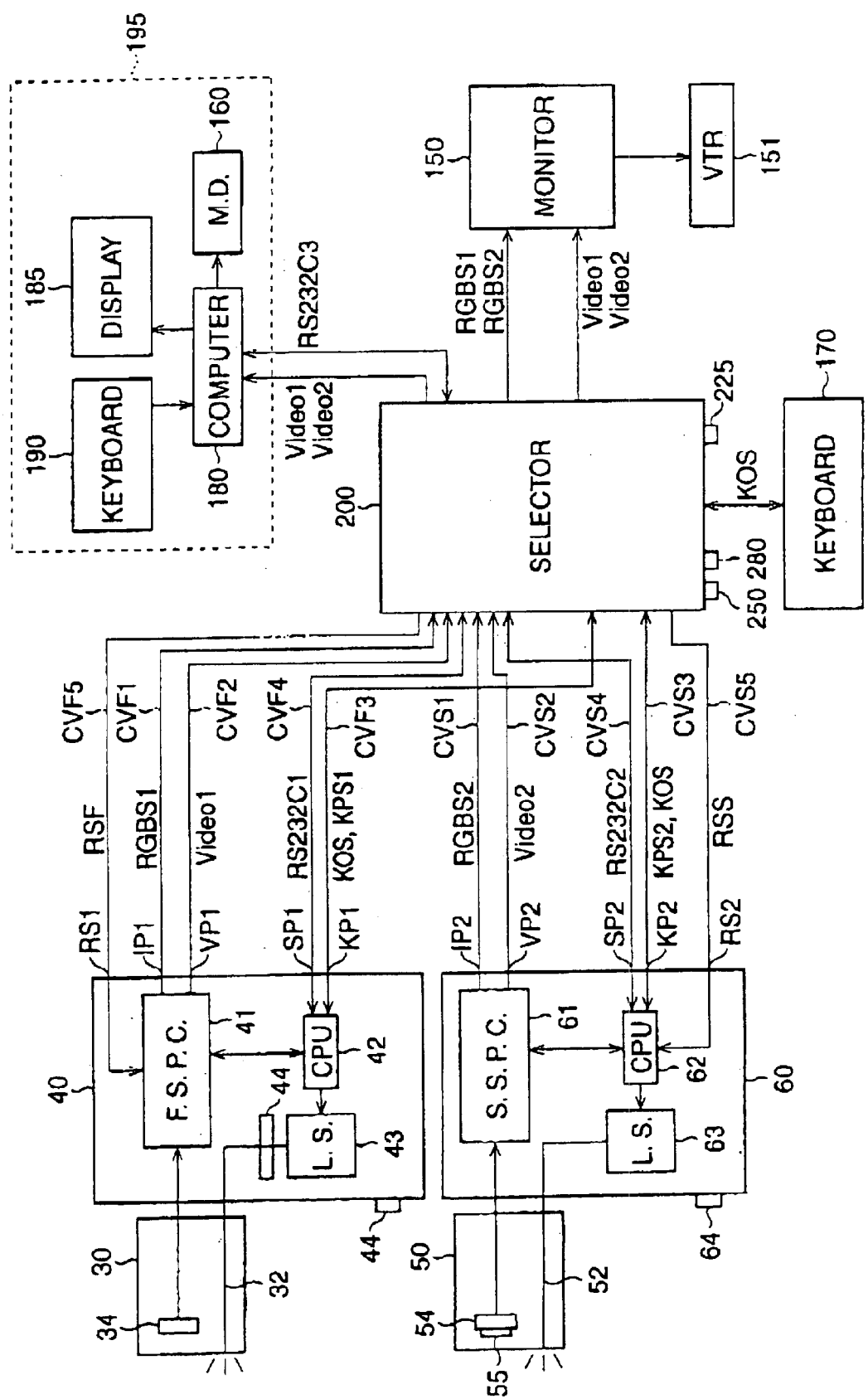
FIG. 1 is a block diagram of an electronic endoscope system of a first embodiment.

FIG. 1 is a block diagram of an electronic endoscope system of the first embodiment.

The electronic endoscope system has a first video-processor 40, a second video-processor 60, a first video-scope 30, a second video-scope 50, a selector 200, a keyboard 170, TV monitor 150 and a computer system 195. The first and second video-scopes 30, 50 are detachably connected to the first and second video-processors 40, 60 respectively, and the first and second video-processors 40, 60 are connected to the selector 200. The selector 200 is connected to the monitor 150, the keyboard 170 and the computer system 195. The first video-processor 40 and the second video-processor 60 turn ON by operating power switches 44, 64, respectively.

For a color photographing process at the first video-scope 30 and the first video-processor 40, the R (Red), G (Green), B (Blue) sequential method is applied. A light source 43 radiating white color light, such as a Halogen lamp, and a rotating filter 44 are provided in the first video-processor 40. The rotating filter 44, composed of Red, Green and Blue color filters, is arranged between the light source 43 and an incident surface of a fiber-optic bundle 32 which transmits light to the distal end of the first video-scope 30. The rotating filter 44 rotates at predetermined revolutions, the white color light passing through the rotating filter 44 is therefore transformed to Red, Green and Blue color light in order. The light passing through the fiber-optic bundle 32 radiates from the distal end of the first video-scope 30, so that an object in the observed area is illuminated by the Red, Green, Blue color light in order.

A CCD (Charge-Coupled Device) 34 of an image sensor is provided at the distal end of the first video-scope 30. R, G, B color light, reflected from the object, reaches the CCD 34 via a object lens (not shown), thus an object image is formed on the CCD 34 and image-pixel signals corresponding to the object image is then generated by photoelectric conversion. The image-pixel signals corresponding to each of the Red, Green, Blue colors are read from the CCD 34 in order and fed to the first video-processor 40.

In the first video-processor 40, a first signal process circuit 41 for processing the image-pixel signals according to the R, G, B sequential method is provided. In the first signal process circuit 41, the image-pixel signals are subjected to various processes, such as white balance, gamma correction, etc, and are then transformed to video signals.

Herein, R, G, B component video signals "RGBS1" and composite video signals "Video1" are generated as the video signals. The R, G, B component video signals "RGBS1" are composed of signals corresponding to Red, signals corresponding to Green, signals corresponding to Blue and synchronizing signals separated respectively, on the other hand, the composite video signals "Video1" are composed of luminance, color difference and composite synchronizing signals. The R, G, B component video signals "RGBS1" are output from a component signal output port IP1, the composite video signals "Video1" are output from a composite signal output port VP1. The component and composite signal output ports IP1, VP1 are connected to the selector 200 via cables CVF1 and CVF2, respectively. Thus, the R, G, B component video signals "RGB1" and the composite video signals "Video1" are fed to the selector 200.

A CPU 42 of the first video-processor 40 is incorporated in a first control circuit (not shown), which is provided in the first video-processor 40 and includes an interface circuit and a memory, etc., and controls the first video-scope 30 and the first video-processor 40. The timing of the signal process executed in the first signal process circuit 41, the timing for reading the image-pixel signals at the CCD 34 and the rotation of the rotating filter 44 are controlled by the CPU 42.

The color photographing process by the second video-scope 50 and the second video-processor 60 uses the color chip filter method. Construction is the same as the first video-scope 30 and the first video-processor 40 except for the color photographing method.

On a photo-sensor area of a CCD 54, provided in the distal end of the second video-scope 50, a color filter 55, checkered by four color elements of Yellow (Y), Magenta (Mg), Cyan (Cy) and Green (G), is arranged. White color Light from a light source 63 passes through an optic-fiber bundle 52, radiates from the distal end of the second video-processor 50 and reflects from the object. Thus, the object image is formed on the CCD 54. In the CCDS 4, image-pixel signals, corresponding to colors passing through the color filter 55, are generated and fed to a second signal process circuit 61 in the second video-processor 60.

In the second signal process circuit 61, based on the image-pixel signals read from the CCD 54, R, G, B component video signals "RGBS2" and composite video signals "Video2" are generated. The R, G, B component video signals "RGBS2" are output from a component signal output port IP2 and the composite video signals "Video2" are output from a composite signal output port VP2. The component and composite signal output ports IP2, VP2 are connected to the selector 200 via cable CVS1, CVS2, respectively. Thus, the R, G, B component video signals "RGB2" and the composite video signals "Video2" are fed to the selector 200. Similarly to the first video-processor 40, A CPU 62 is incorporated in a second control circuit (not shown), which is provided in the second video-processor 60 and includes an interface circuit (not shown), etc., and controls the second video-scope 50 and the second video-processor 60.

The selector 200, connected to the monitor 150, the computer system 195 and the keyboard 170, selects either the video-processor 40 or the video-processor 60. Namely, the selector 200 selectively feeds the R, G, B component video signals "RGB1" and the composite video signals "Video1" from the first video-processor 40 or the R, G, B component video signals "RGB2" and the composite video signals "Video2" from the second video-processor 60. Based on the state of the first and second video-processors 40, 60, the selector 200 automatically selects the first video-processor 40 or the second video-processor 60. A selecting push switch 225, provided on the selector 200, is a manually operated to select either the video-processor 40 or the video-processor 60. Further, on the selector 200, a first indicator lamp 250 and a second indicator lamp 280 are provided.

When the video-processor 40 is selected, the R, G, B component video signals "RGBS1" and the composite video signals "Video1", output from the component signal output port IP1 and the composite signal output port VP1 respectively, are fed to the monitor 150 via the selector 200. In this embodiment, based on the R, G, B component video signals "RGBS1", the color object image is displayed on the monitor 150. A VTR (Video Tape Recorder) 151, for recording the object image, is connected to the monitor 150.

When the second video-processor 60 is selected, the R, G, B component video signals "RGBS2" and the composite video signals "Video2", output from the component signal output port IP2 and the composite signal output port VP2 respectively, are fed to the monitor 150 via the selector 200. Then, based on the R, G, B component video signals (RGBS2), the color object image is displayed on the monitor 150.

The keyboard 170 is connected to the selector 200 and the first and second video-processors 40, 60 are connected to the selector 200 via cables CVF3, CVS3, respectively. The keyboard 170 operates the first video-processor 40 or the second video-processor 60, selected by the selector 200. For example, to display the information associated with the object image on the monitor 150, a contour correcting process to the displayed object image and soon, is performed using the keyboard 170. A keyboard operating signal "KOS", generated by operating the keyboard 170, is fed to one of the first and second video-processors 40, 60.

When the first video-processor 40 is selected, the keyboard operating "KOS" is input to a keyboard port KP1 on the first video-processor 40 and fed to the CPU 42 via the interface circuit in the first video-processor 40. On the other hand, when the second video-processor 60 is selected, the keyboard operating signal "KOS" is input to a keyboard port KP2 on the second video-processor 60 and fed to the CPU 62 via the interface circuit in the second video-processor 60. Further, as described later, first and second electric power signals "KPS1" and "KPS2" are output from the first control circuit in the first video-processor 40 and the second control circuit in the second video-processor 60 and then fed to the selector 200 via the cables CVF3, CVS3, respectively. Note that, an electric power for the keyboard 170 is supplied from an electric power supplying circuit (not shown) provided in the selector 200.

The computer system 195, used as a filing system, is composed of a computer 180, a keyboard 190, a monitor 185 for the computer 180 and a memory device 160, such as a MO (Magnetic Optical Disk). The computer 180 is connected to the selector 200. The keyboard 190, the monitor 185 and the memory device 160 are connected to the computer 180. The composite video signals "Video1" or the composite video signals "Video2" is output from the selector 200 to the computer 180, in which the composite video signal "Video1" or the composite video signals "Video2" is subjected to compressing process and is fed to the memory device 160, in which the still object image is stored.

In the first video-processor 40, data associated with the object image, such as still object image data, patient data and so on, is output from a serial port SP1 on the first video-processor 40 as serial data "RS232C1". Note that, the outputting of the serial data "RS232C1" is controlled by the CPU 42. When the first video-processor 40 is selected, the serial data "RS232C1" is fed to the selector 200 via a cable CVF4 and is then fed to the computer 180. The serial data "RS232C1" is recorded in the memory device 160. After the examination or operation is terminated, the filing is performed in the computer system 195, using the keyboard 190. On the other hand, when the second video-processor 60 is selected, serial data "RS232C2" is output from a serial port SP2 on the second video-processor 60 to the selector 200 via a cable CVS4 and is then fed to the computer 180, similar to serial data "RS232C1".

Note that, serial data "RS232C3" is fed from the computer 180 to the first video-processor 40 or the second video-processor 60 via the selector 200, by operating the keyboard 190.

The first video-processor 40 and the second video-processor 60 are reset by a reset signal "RSF" and a reset signal "RSS" fed from the selector 200, respectively. The reset signal "RSF" for resetting the first video-processor 40 is input to a reset port RS1 on the first video-processor 40 via a cable CVF5. The re set signal for resetting the second video-processor 60 is input to a reset port RS2 on the second video-processor 60 via a cable CVS5.

Figure 2:
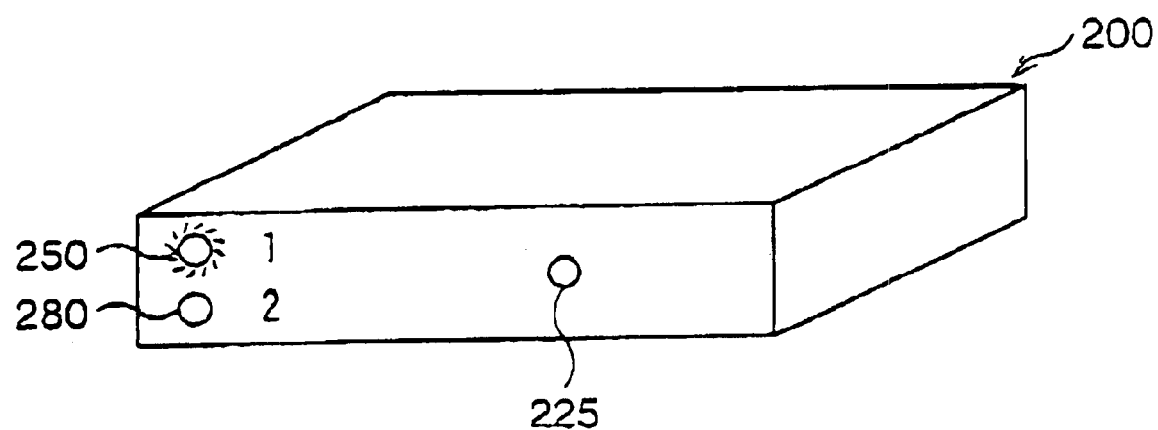
FIG. 2 is a perspective view showing the selector of the first embodiment.

FIG. 2 is a perspective view showing the selector 200.

As shown in FIG. 2, on a front surface of the selector 200, the selecting push switch 225, the first indicator lamp 250 and the second indicator lamp 280 which are LEDs (Luminance Emit Diodes), are provided. The first indicator lamp 250 indicates that the video-processor 40 is selected by the selector 200, namely, the object image displayed on the monitor 150 is based on the R, G, B component video signals "RGBS1". The second indicator lamp 280 indicates that the video-processor 60 is selected. Note that, on the back surface of the selector 200, a plurality of ports (not shown) for connecting the computer 180 and the monitor 150 to the first and second video-processors 40, 60 and connecting the keyboard 170 to the first and second video-processors 40, 60, are provided.

Figure 3:
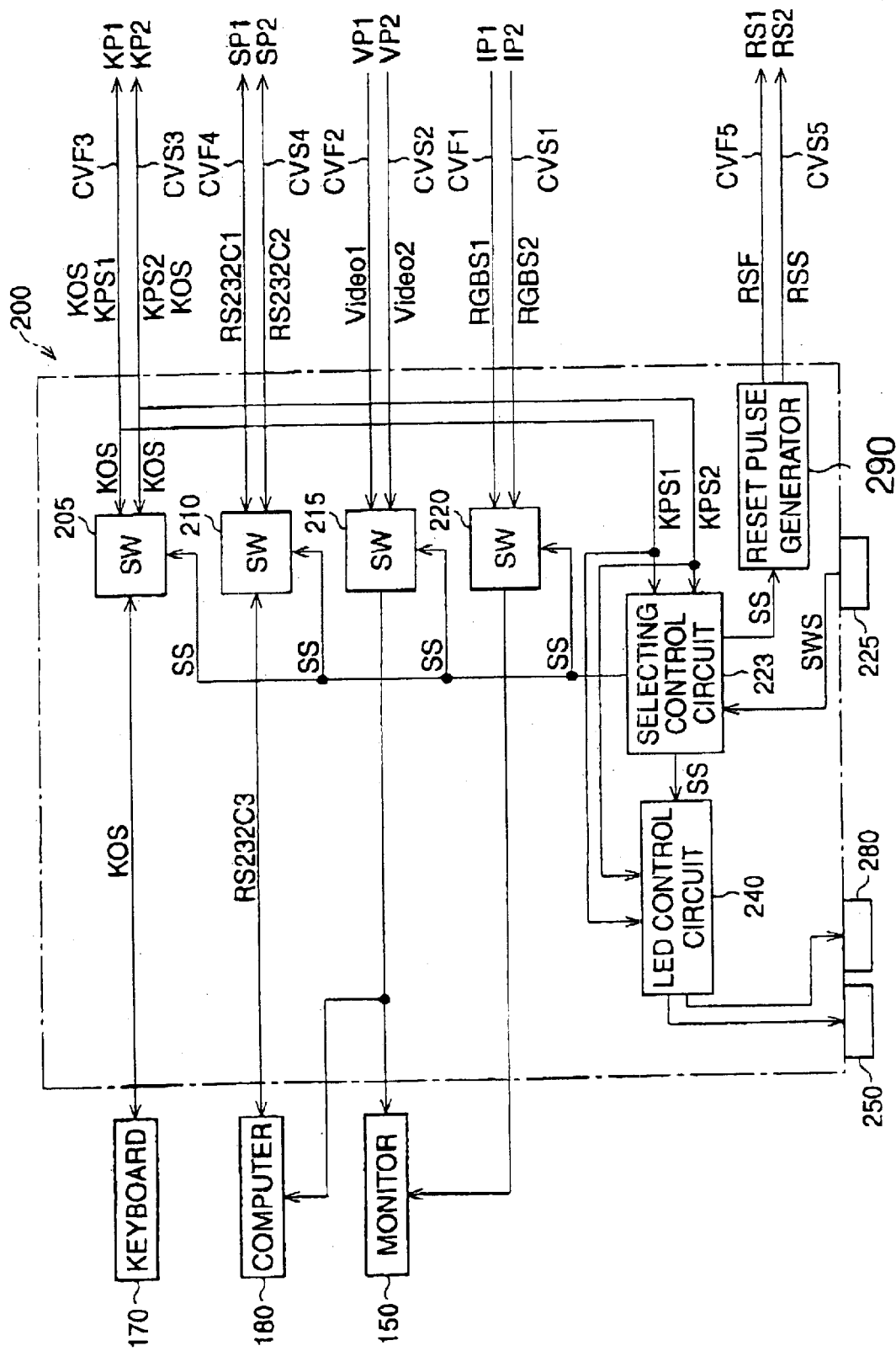
FIG. 3 is a block diagram of the selector of the first embodiment.

FIG. 3 is a block diagram of the selector 200.

The selector 200 has four switch circuits 205, 210, 215, 220, a selecting control circuit 223, an LED control circuit 240 and a reset pulse generator 290. The four switch circuits 205, 210, 215, 220 are connected to the selecting control circuit 223. Further, the selecting push switch 225, the reset pulse generator 290 and the LED control circuit 240 are also connected to the selecting control circuit 223.

The switch circuit 205, which receives the keyboard operating signal "KOS", is switched so that the keyboard operating signal "KOS" from the keyboard 170 is fed to the first video-processor 40 or the second video-processor 60. The switch circuit 210, which receives the serial data "RS232C1" from the first video-processor 40 and the serial data "RS232C2" from the second video-processor 60, is switched such that either the serial data "RS232C1" or the serial data "RS232C2" is fed to the computer 180. Further, the serial data "RS232C3" from the computer 180 is fed to the first video-processor 40 or the second video-processor 60 via the switch circuit 210.

The switch circuit 215, which receives the composite video signals "video1" from the first video-processor 40 and the composite video signals "Video2" from the second video-processor 60, is switched such that either the composite video signals "Video1" or the composite video signals "Video2" is fed to the computer 180 and the monitor 150. The switch circuit 220, which receives the R, G, B component video signals "RGB1" from the first video-processor 40 and the R, G, B component video signals "RGB2" from the second "video-processor 60, is switched such that either the R, G, B component video signals "RGB1" or the R, G, B component video signals "RGB2" is fed to the monitor 150.

The first electric power signal "KPS1" is fed from the first video-processor 40 via the cable CVF3 and the second electric power signal "KPS2" is fed from the second video-processor 60 via the cable CVS3. The first and second electric power signals KPS1", "KPS2" are input to the selecting control circuit 223 and the LED control circuit 240, respectively. When the first video-processor 40 is turned ON, the first electric power signal "KPS1" is at a "High" level. On the other hand, when the first video-processor 40 is turned OFF, the first electric power signal "KPS1" is at a "Low" level. The second electric power signal "KPS2" fed from the second video-processor 60 is also set to "High" or "Low" level, similar to the first electric power signal "KPS1".

Based on the first and second electric power signals "KPS1", "KPS2", a selecting signal "SS" is fed from the selecting control circuit 223 to the four switch circuits 205, 210, 215, 220, the LED control circuit 240 and the reset pulse generator 290. The four switch circuits 205, 210, 215, 220 are switched in accordance with the level of the selecting signal "SS". When the first video-processor 40 is selected, the four switches 205, 210, 215, 220 are switched such that the R, G, B component video signals "RGBS1" are fed to the monitor 150, the composite video signals "Video1" are fed to the monitor 150 and the computer 180 and the keyboard operating signal "KOS" is fed to the first video processor 40. On the other hand, when the second video-processor 60 is selected, the four switches 205, 210, 215, 220 are switched such that the R, G, B component video signals "RGBS2" are fed to the monitor 150, the composite video signals "Video2" are fed to the monitor 150 and the computer 180 and the keyboard operating signal "KOS" is fed to the second video-processor 60.

When the selecting push button 225 is operated, an operating signal "SWS" is fed to the selecting control circuit 223 and consequently a selecting signal "SS" is output from the selecting control circuit 223.

Figure 4:
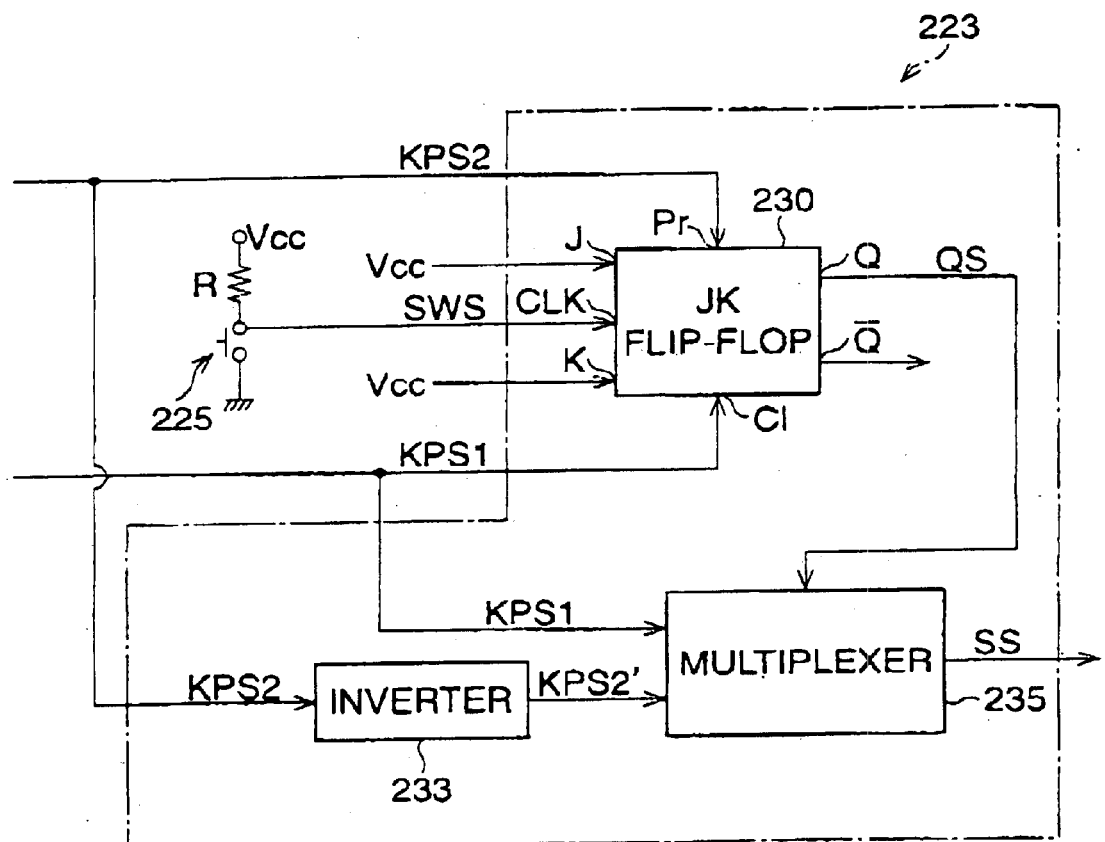
FIG. 4 is a block diagram of the selecting control circuit shown in FIG. 3.

FIG. 4 is a block diagram of the selecting control circuit 223 shown in FIG. 3, and FIGS. 5 and 6 are a tables indicating the relationship between the first and second electric power signals "KSP1", "KSP2", the operating signal "SWS" and the selecting signal "SS".

The selecting control circuit 223 has a JK flip-flop 230, an inverter 233 and a multiplexer 235, as shown in FIG. 4. The JK flip-flop 230 has J and K inputs, outputs (Q and /Q), clock input CLK and a synchronous present and clear inputs Pr, Cl. Note that, herein, the output "/Q" represents the inverted output "Q". The first electric power signal "KSP1" is input to the clear input Cl, while the second electric power signal "KSP2" is input to the preset input Pr. A voltage Vcc is input to the J, K inputs and the operating signal "SWS" is input to the clock input CLK. When the selecting push button 225 is pushed once, the operating signal "SWS" is input to the clock input CLK as one clock pulse signal. The JK flip-flop 230 outputs a state signal "QS" to the multiplexer 235. The level of the state signal "QS" depends upon an input of the operating signal "SWS" to the clock input CLK and the level of the clear, preset inputs Cl, Pr, or the level of the first and second electric power signals "KSP1", "KSP2".

The inverter 233 inverts the level of the second electric power signal "KSP2". Thus, the second electric power signal "KSP2" is inverted from "High" to "Low" level or from "Low" to "High" level. Herein, an inverted second electric power signal is represented by "KPS2'". In the multiplexer 235, the first electric power signal "KPS1", the inverted second electric power signal "KPS2'" are input with the state signal "QS".

The multiplexer 235 selectively outputs ether the inverted second electric power signal "KSP2'" or the first electric power signal "KSP1" in accordance with the level of the state signal "QS". The invert second electric power signal "KSP2'" or the first electric power signal "KSP1" is fed to the four switch circuits 205, 210, 215, 220, the LED control circuit 240 and the reset pulse generator 290 as the selecting signal "SS", as shown in FIG. 3. When the state signal "QS" is "High", the inverted second electric power signal "KSP2'" is output from the multiplexer 235 as the selecting signal "SS", on the other hand, when the state signal "QS" is "Low", the first electric power signal "KSP1" is output as the selecting signal "SS".

Based on the level of the state signal "SS" fed from the multiplexer 235, i.e., the level of the first electric power signal "KSP1" or the inverted second electric power signal "KSP2'", the four switches 205, 210, 215, 220 are switched. When the selecting signal "SS" is "High", the first video-processor 40 is selected and when the selecting signal "SS" is "Low", the second video-processor 60 is selected.

The JK flip-flop 230 is a falling-edge triggered flip-flop with a synchronous preset and clear inputs Pr, Cl. The preset input Pr is a "low-active" input, namely, the preset input Pr accepts a signal only when the signal is "Low" level. The clear input Cl is also the same as the preset input Pr. While the switching push button 225 is not operated, i.e., the operating signal "SWS" is not input to the clock input CLK as the one clock pulse signal and the operating signal "SWS" remains at a "High" or "Low" level. The level of the state signal "QS" is determined in accordance with the levels of the first and second electric power signals "KSP1", "KSP2". When the operating signal "SWS" of one clock pulse signal is input to the clock input CLK, the state of the JK flip-flop 230 is transited at the trailing edge of the clock pulse signal.

In FIG. 5, the selected video-processor of the first and second video-processors 40, 60 in a case when the first video-processor 40 is turned ON first, is shown. At the initial state, when the first and second video-processor power switches 44, 64 are not turned ON, the first and second electric power signals "KPS1", "KPS2" are both "Low" level. While the selecting push switch 225 is not operated, the operating signal "SWS" input to the clock input Cl is "High". When the first and second electric power signals "KPS1", "KPS2" are both "Low", the state of the JK flip-flop 230 becomes active, namely, the state signal "QS" becomes "High". Then, when the state signal "QS" is "High", the multiplexer 235 selects and outputs the inverted second electric power signal "KSP2'" as the selecting signal "SS". As the second electric power signal "KSP2" is "Low", the inverted second electric power signal "KSP2'" is "High". Namely, the selecting signal "SS" becomes "High" level. As described above, when the selecting signal "6S" is "High", the first video-processor 40 is selected.

When the first video-processor 40 is turned ON first, the first electric power signal "KPS1", input to the clear input Cl, becomes "High" level. When the first electric power signal "KSP1" input to the clear input Cl and the second electric power signal "KSP2" input to the preset input Pr are "High" and "Low" respectively, the state signal "QS" becomes "High". As the multiplexer 235 selects the inverted second electric power signal "KSP2'", similar to the initial state, the selecting signal "SS" becomes "High", namely, the first video-processor 40 is selected.

When the second video-processor 60 is turned ON after first video-processor 40, the first and second electric power signals "KSP1", "KSP2" become "High". As the state of the JK flip-plop 230 does not change when the first and second electric power signals "KSP1", "KSP2" are both "High", the state signal "QS" is maintained at the "High" level. Therefore, the multiplexer 235 selects the inverted second electric power signal "KSP2'". Since the second electric power signal "KSP2" is "High", the inverted second electric power signal "KSP2'" becomes "Low". When the selecting signal "SS" is "Low", the second video-processor 60 is selected.

When the selecting push button 225 is pushed when the first and second video-processors 40, 60 are turned ON, the JK flip-flop 230 outputs the state signal "QS" in accordance with the J, K inputs. As the J, K inputs are both "High", the state of the JK flip-flop 230 changes. Namely, the level of the state signal "QS" is inverted from the preceding state. Therefore, the state signal "QS" is changed from "High" to "Low". As the state signal "QS" is "Low", the multiplexer 235 selects the first electric power signal "KSP1", namely, the selecting signal "SS" output from the multiplexer 235 becomes "High". Thus, the first video-processor 40 is selected.

When the selecting push button 225 is pushed again, the state of the JK flip-flop 230 reverts to the previous state. As the preceding level of the state signal "QS" is "Low" level, the state signal "QS" becomes "High" level, so that the multiplexer 235 selects the inverted second electric signal "KSP2'". As the selecting signal "SS" is "Low" level, the second video-processor 60 is selected. In a state that the first and second video-processors 40, 60 are turned ON, the video-processors are switched alternately every time the selecting push switch is pushed.

FIG. 6 is a table showing the process when the second video-processor 60 is firstly turned ON first. In the initial state, the first video-processor 40 is selected. When the second video-processor 60 is turned ON first, the second electric power signal "KPS2" becomes "High". When the first electric power signal "KPS1" is "Low" and the second electric power signal KPS2 is "High", the state signal "QS" becomes "Low". Therefore, the multiplexer 235 selects and outputs the first electric power signal "KPS1". As the first electric power signal "KPS1" is "Low", the selecting signal "SS" becomes "Low". Namely, the second video-processor 60 is selected.

When the first video-processor 40 is turned ON after the second video-processor 60, the first and second electric power signals "KSP1", "KSP2" become "High". As the state of the JK flip-flop 230 does not change when the first and second electric power signal "KSP1", "KSP2" become "High", the state signal "QS" remains at a "Low" level and the multiplexer 235 selects the first electric power signal "KSP1". The first electric power signal "KSP1" is "High", so the selecting signal "SS" becomes "High". Namely, the first video-processor 40 is selected.

When the selecting push button 225 is pushed again, the state of the JK flip-flop 230 transits, so that the state signal "QS" is inverted from "Low" to "High". As the second electric power signal "KSP2" is "High" level, the selecting signal "SS" output from the multiplexer 235 becomes "Low", namely, the second video-processor 60 is selected. When the selecting push switch 225 is further pushed, the first video-processor 40 is selected.

Figure 7:
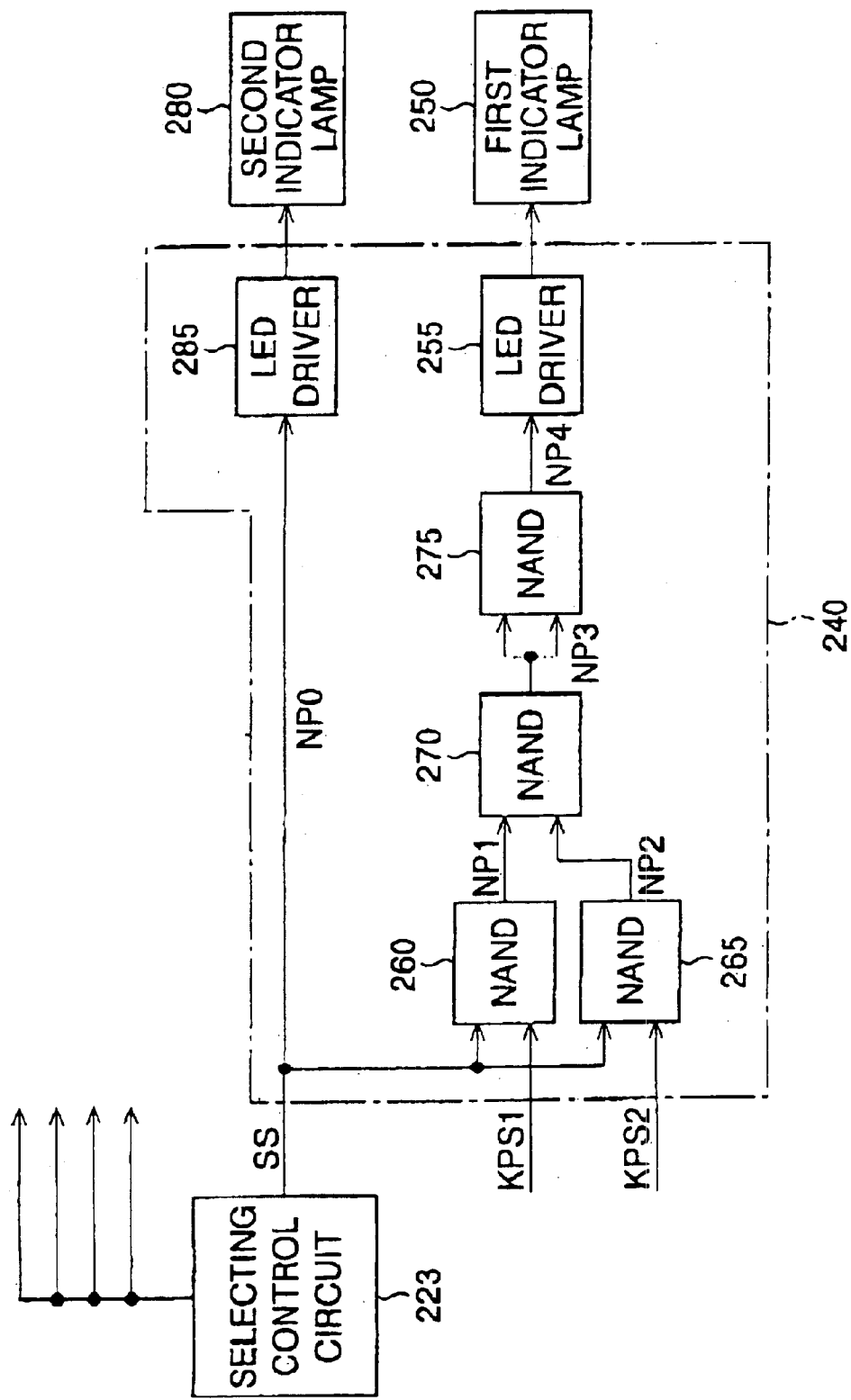
FIG. 7 is a block diagram of an LED control circuit shown in FIG. 3.

FIG. 7 is a block diagram of the LED control circuit 240 shown in FIG. 3.

The LED control circuit 240 has two LED drivers 255, 285 and four NAND circuits 260, 265, 270, 275. The selecting signal "SS" is input to the LED driver 285 as a pulse signal NP0 and is input to the NAND circuit 260, 265. Further, the first electric power signal "KPS1" is input to the NAND circuit 260, the second electric power signal "KPS2" is input to the NAND circuit 265.

The NAND circuit 260 and the NAND circuit 265 output pulse signals "NP1" and "NP2" respectively. The pulse signals "NP1", "NP1" are then input to the NAND circuit 270. The NAND circuit 270 outputs a pulse signal "NP3". The pulse signal "NP3" is divided into two pulse signals and input to the NAND circuit 275. The NAND circuit 275 outputs a pulse signal "NP4". The pulse signal "NP4" is input to the LED driver 255. Each of the NAND circuits 260, 265, 270, 275 outputs "High" level signal unless the input signals are both "High". When the input signals are both "High", each of the NAND circuits 260, 265, 270, 275 outputs a "Low" level signal.

The LED driver 255 and the LED driver 285 turn ON or OFF the first indicator lamp 250 and the second indicator lamp 280 in accordance with the level of the pulse signals "NP0", "NP4", respectively. The LED drivers 255, 285 illuminate the first indicator lamp 250 and the second indicator lamp 280 when the pulse signal "NP0" and the pulse signal "NP4" are "Low". On the other hand, the LED drivers 255, 285 turn OFF the first indicator lamp 250 and the second indicator lamp 280 when the pulse signal "NP0" and the pulse signal "NP4" are "High".

FIG. 8 is a table T3 indicating the state of the first and second indicator lamps 250, 280 when the first video-processor 40 is turned ON first.

At the initial state, the first and second electric power signals "KPS1", "KPS2" are both "Low" and the selecting signal "SS" is "High". Therefore, the pulse signal "NP1" output from the NAND circuit 260, and the pulse signal "NP2" output from the NAND circuit 265, become "High". As the pulse signals "NP1", "NP2" are both "High", the pulse signal "NP3", output from the NAND circuit 270, becomes "Low". As the two pulse signals "NP3" are "Low" when input to the NAND circuit 275, the pulse signal "NP4" output from the NAND circuit 275 becomes "High". Therefore, as the pulse signals "NP0", "NP4" are both "High", the first and second indicator lamps 250, 280 are not illuminated at the initial state.

When the first video-processor 40 is turned ON, the electric power signal "KPS1" becomes "High", namely, the pulse signal "NP0" becomes "High". As the first electric power signal "KPS1" and the selecting signal "SS" are "High", the pulse signal "NP1" becomes "Low". Therefore, the pulse signal "NP3" output from the NAND circuit 270 becomes "High" and the pulse signal "NP4" becomes "Low". As the pulse signals "N0", "N4" are "High" and "Low" respectively, the first indicator lamp 250 is illuminated.

When the second video-processor 60 is turned ON after the first video-processor 40, the first and second electric power signals "KPS1", "KPS2" become "High" and the selecting signal "SS" becomes "Low". Therefore, the pulse signal "NP0" is "Low", the pulse signals "NP1", "NP2" become "High" level, the pulse signals "NP3" become "Low" and the pulse signal "NP4" becomes "High". As the pulse signals "NP0", "NP4" are "Low" and "High" respectively, the second indicator lamp 280 is illuminated and the first indicator lamp 250 is turned OFF.

When the selecting push button 225 is pushed, the selecting signal "SS" becomes "High", so that the pulse signals "NP0", "NP1", "NP2", "NP3" become "High", "Low", "Low", "High" respectively and the pulse signal "NP4" becomes "Low". As the pulse signals "NP0", "NP4" are "High" and "Low" level respectively, the first indicator lamp 250 is turned ON and the second indicator lamp 280 is turned OFF.

When the selecting push button 225 is pushed again, the selecting signal "SS" becomes "Low". Therefore, the pulse signals "NP1", "NP2" become "High", the pulse signal "NP3" becomes "Low" and the pulse signal "NP4" becomes "High". As the pulse signals "NP0", "NP4" are "Low" and "High" respectively, the first indicator lamp 250 is turned OFF and the second indicator lamp 280 is turned ON.

FIG. 9 is a table T4 indicating the state of the first and second indicator lamps 250, 280 when the second video-processor 60 is turned ON first.

As shown in the table T4, when the second-video-processor 60 is turned ON first, the pulse signal "NP0" becomes "Low" and the pulse signal "NP4" becomes "High". Therefore, only the second indicator lamp 280 is illuminated. When the first video-processor 40 is turned ON after the second video-processor 60, the pulse signal "NP0" becomes "High" and the pulse signal "NP4" becomes "Low". Therefore, the second indicator lamp 280 is turned OFF and the first indicator lamp 250 is illuminated. When the selecting push switch 225 is pressed, the second indicator lamp 280 is turned ON and the first indicator lamp 250 is turned OFF. When the selecting push switch 225 is pressed again, the second indicator lamp 280 is turned OFF and the first indicator lamp 250 is turned ON.

Figure 10:
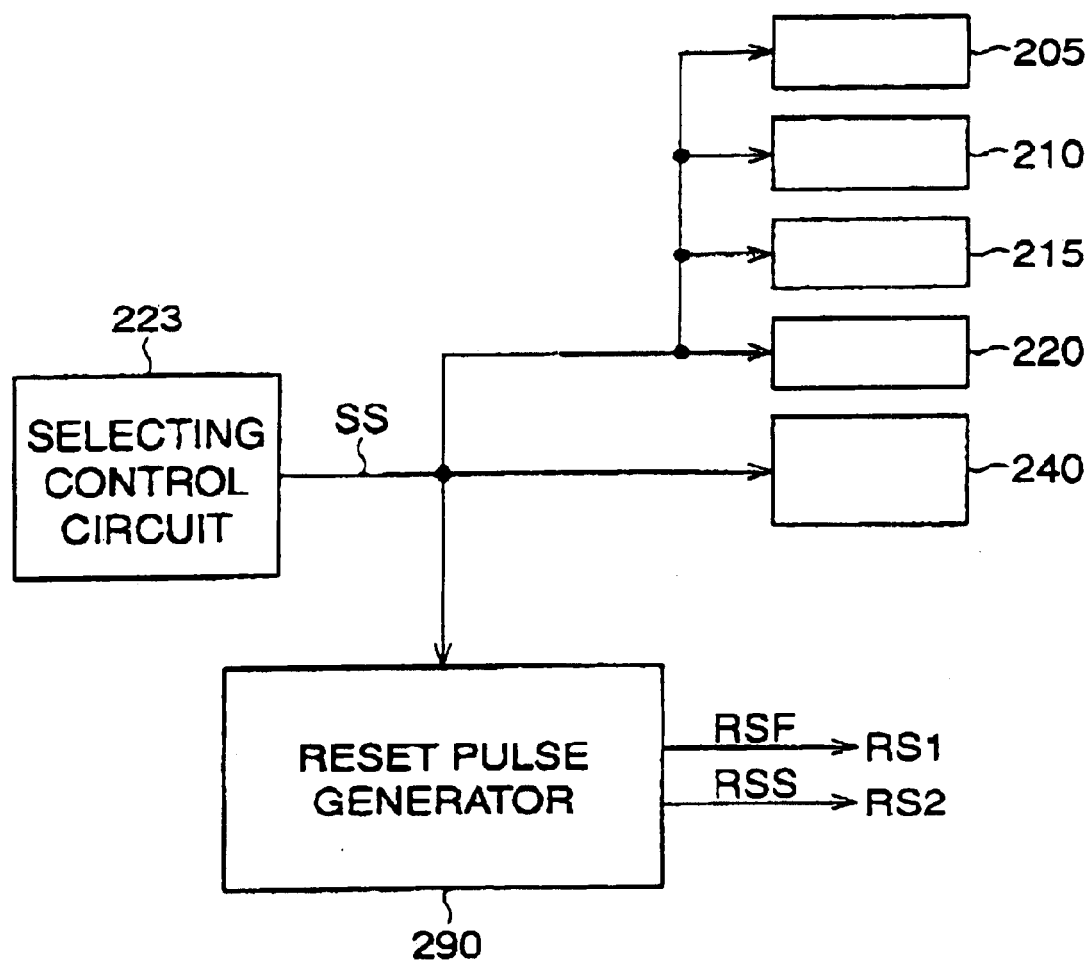
FIG. 10 is an enlarged view of portion of block diagram of FIG. 3 associated with the reset pulse generator 290.

FIG. 10 is an enlarged view of portion of block diagram of FIG. 3 associated with the reset pulse generator 290. Herein, the reset pulse generator 290 is a multivibrator.

The selecting signal "SS", fed from the selecting control circuit 223, is input to the reset pulse generator 290. When the level of the selecting signal "SS" changes from "Low" to "High", the selected-processor is switched from the second video-processor 60 to the first vide-processor 40 and the reset signal "RSF" is fed from the reset pulse generator 290 to the first video-processor 40 via the cable CVF5. On the other hand, when the level of the selecting signal "SS" changes from "High" to "Low", the selected-processor is switched from the first video-processor 40 to the second vide-processor 60 and the reset signal "RSS" is fed to the second video-processor 60 via the cable CVS5.

As described above, in the first embodiment, the selector 200 selects either the first video-processor 40 or the second video-processor 60, according to the operating state of the first and second video-processors 40, 60 or by activating of the selecting push switch 225. Namely, the selector 200 selectively feeds either the component R, G, B video signals "RGB1" and the composite, video signal "Video1" from the first video-processor 40 or the component R, G, B video signals "RGB2" and the composite video signal "Video2" from the second video-processor 60, to the monitor 150. Further, the selector 200 selectively feeds either the serial data "RS232C1" and the composite video signal "Video1" from the first video-processor 40, or the serial data "RS232C2" and the composite video signal "Video2" from the second video-processor 60, to the computer system 195. When the first video-processor 40 is selected, the first indicator lamp 250 is illuminated and when the second video-processor 60 is selected, the second illuminator lamp 280 is illuminated. The selected video-processor is operated by using the keyboard 170.

In the first embodiment, the color photographing process differs between the first video-processor 40 and the second video-processor 60. However, the color photographing process of the first video-processor 40 may also the same as that of the second video-processor 60.

A plurality of video-processors, more than two, may be provided in an electronic endoscope system. In this case, the selector 200 is connected to the plurality of the video-processors and selects one of the plurality of the video-processors. When only one video-processor is turned ON, the selector selects the video-processor which is turned ON. When at least two video-processors are turned ON, the selector 200 selects a video-processor, which was turned ON last from among the plurality of video-processors. Further, a selecting switch for selecting one of the plurality of video-processors may be provided on the selector 200. Then, a plurality of indicator lamps, the number of which corresponds to the number of video-processors, are provided on the selector 200, one of the plurality of indicator lamps, corresponding to the selected video-processor, is illuminated.

Other input device, for example, a joystick, maybe applied is in place of the keyboard 170. In this case, the first and second electric power signals "KSP1", "KSP2" are transmitted to the selector 200 via cables, which connect the selector 200 to the plurality of video-processors and transmits input device operating signal generated by operating the input device to the selected video-processor among the plurality of video-processors.

A neon lamp may be provided on the selector 200 in place of the first and second indicator lamps 250, 280, which are LED lamps. Further, an LCD (Liquid Crystal Device) for displaying the selected video-processor may be provided on the selector 200.

With reference to FIGS. 11 to 23, an electronic endoscope system of the second embodiment is explained.

The second embodiment is different from the first embodiment in that an indicator for indicating the selected video-processor is provided on the keyboard and a setting switch for setting of types of video-processors is provided. Since the reminder of the second embodiment is similar to that of the first embodiment, designations remain the same.

Figure 11:
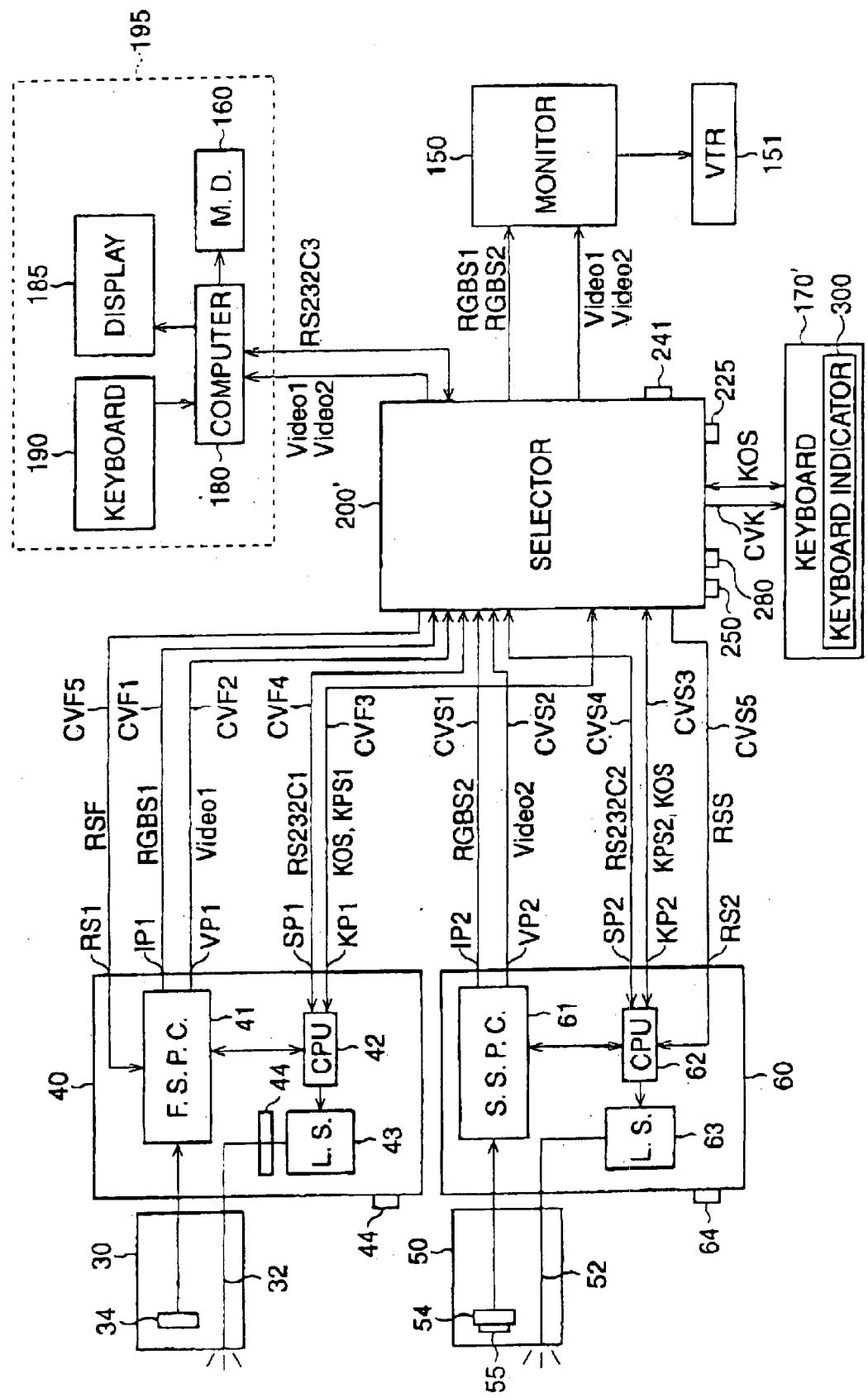
FIG. 11 is a block diagram of the electronic endoscope system of a second embodiment.

FIG. 11 is a block diagram of the electronic endoscope system including a selector 200' and a keyboard 170' of the second embodiment. A setting switch 241 provided on the selector 200' is a switch for registering the type of video-processor. As described later, the type of video-processor is set by operating the setting switch 241. In the keyboard 170', a keyboard indicator 300 for indicating the selected video-processor is provided. The keyboard indicator 300 is connected to the selector 200' via an indicating circuit cable CVK.

Figure 12:
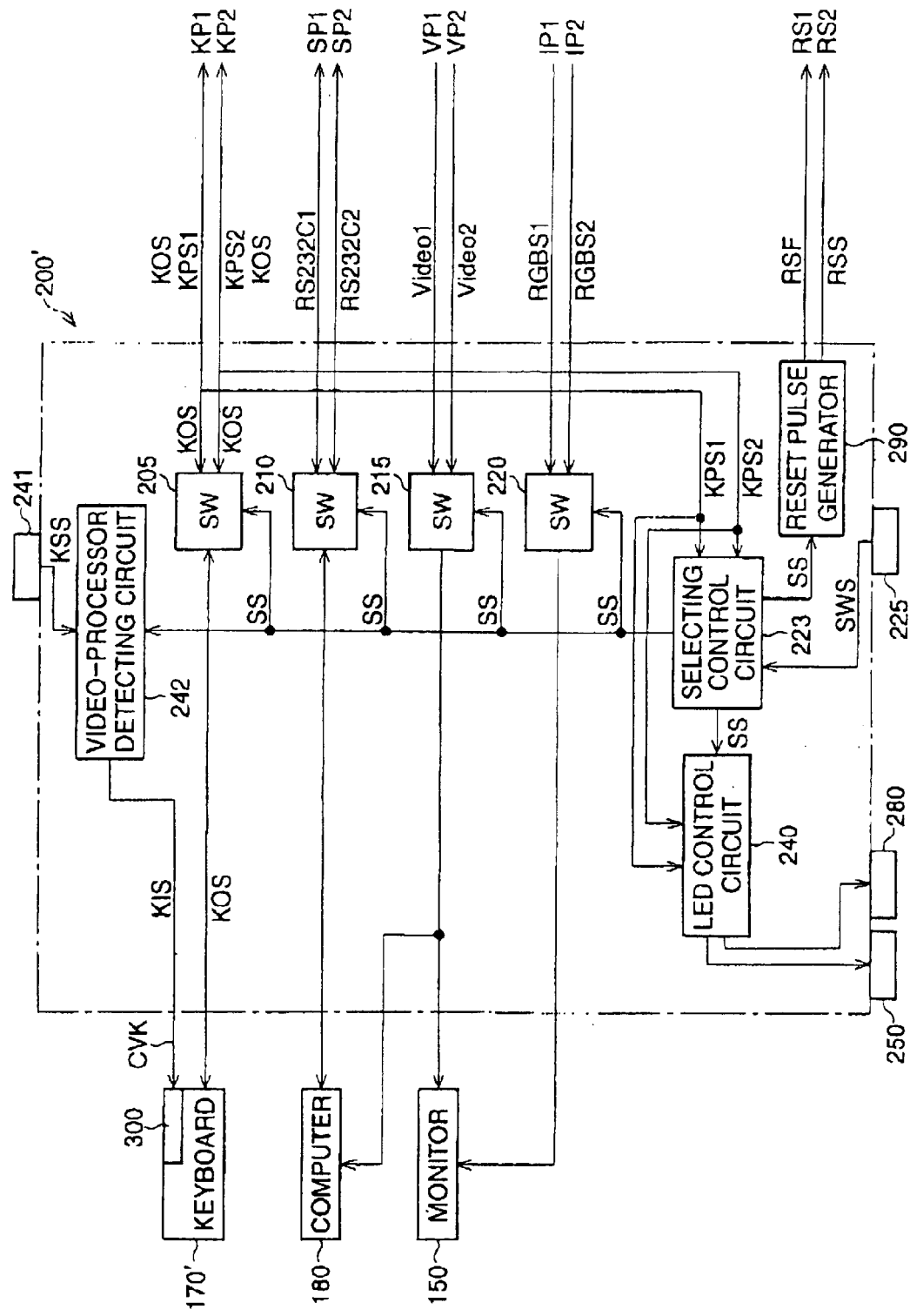
FIG. 12 is a block diagram of the selector of the second embodiment.

FIG. 12 is a block diagram of the selector 200'.

The selector 200' has a video-processor detecting circuit 242, connected to the selecting control circuit 223 and the keyboard indicator 300 in the keyboard 170'. When the setting switch 241 is operated, a video-processor setting signal "KSS" is fed to the video-processor detecting circuit 242. Based on the video-processor setting signal "KSS" and the selecting signal "SS" fed from the selecting control circuit 223, an indicating signal "KIS" is output from the video-processor detecting circuit 242 to the keyboard indicator 300. Then, based on the indicating signal "KIS", the selected video-processor is indicated at the keyboard indicator 300.

Figure 13:
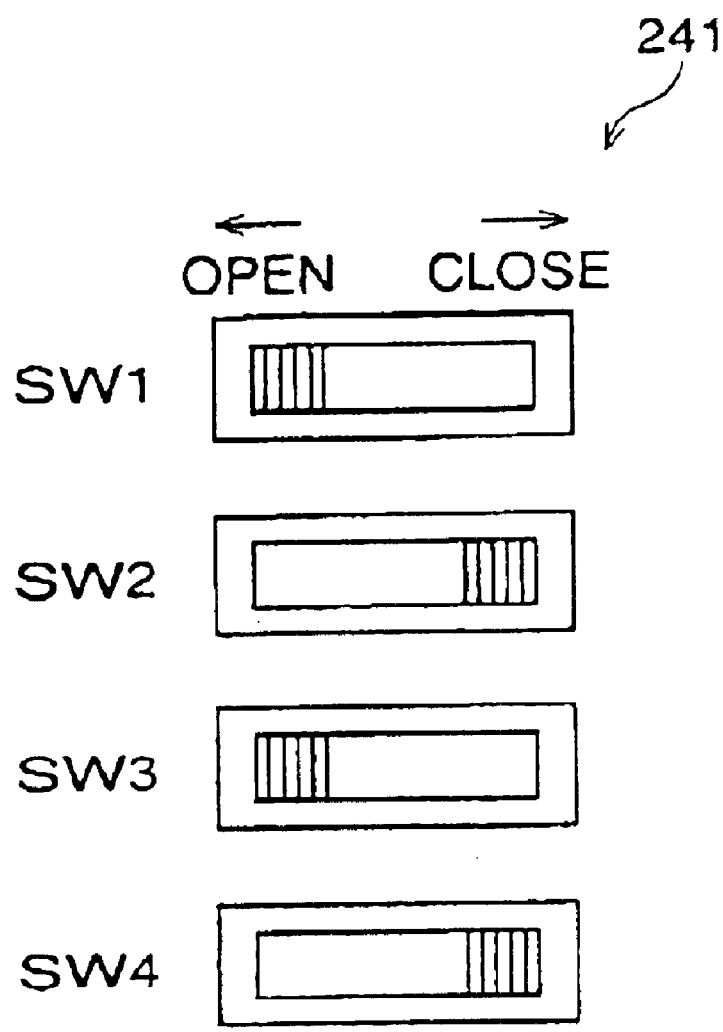
FIG. 13 is a view showing the setting switch.

FIG. 13 is a view showing the setting switch 241.

In this embodiment, four kinds of video-processors in accordance with the R, G, B sequential method are prepared in advance and one of the four video-processors is connected to the selector 200' as a first video-processor 40. The four video-processors are different with respect to the model types, which reflect their time of manufacture. Similarly, four kinds of video-processors in accordance with the color chip filter method are prepared in advance and one of the four video-processors is connected to the selector 200' as a second video-processor 60. In this embodiment, there are four different types of video-processors that correspond to the R, G, B sequential method "VPFA", "VPFB", "VPFC", "VPFD" and there are four different types of video-processors that correspond to the color chip filter method "VPSA", "VPSB", "VPSC", "VPSD". Hereinafter, the type names of the four video-processors corresponding to the R, G, B sequential method are represented by "VPFA", "VPFB", "VPFC", "VPFD", respectively, and the type names of the four video-processors corresponding to the color chip filter method are represented by "VPSA", "VPSB", "VPSC", "VPSD", respectively.

The setting switch 241 has four slide switches SW1, SW2, SW3, SW4. The slide switches SW1, SW2 are switches for registering the type of first video-processor 40 corresponding to the R, G, B sequential method and the slide switches SW3, SW4 are for registering the type of second video-processor 60 corresponding to the color chip filter method.

FIG. 14 is a table T5 indicating the position of the four slide switches SW1, SW2, SW3, SW4 and the various types of first and second video-processors 40, 60.

As shown in the table T5, the type of the first video-processor 40 and the type of the second video-processor 60 correspond to an open-close state of the slide switches SW1, SW2 and an open-close state of the slide switches SW3, SW4, respectively. For example, when the first video-processor 40 of the type-name "VPFC" and the second video-processor 60 of the type-name "VPSC" are connected to the selector 200', the state of switches SW1, SW2, SW3, SW4 are set to "open", "close", "open", "close" respectively, as shown in FIG. 13.

Figure 15:
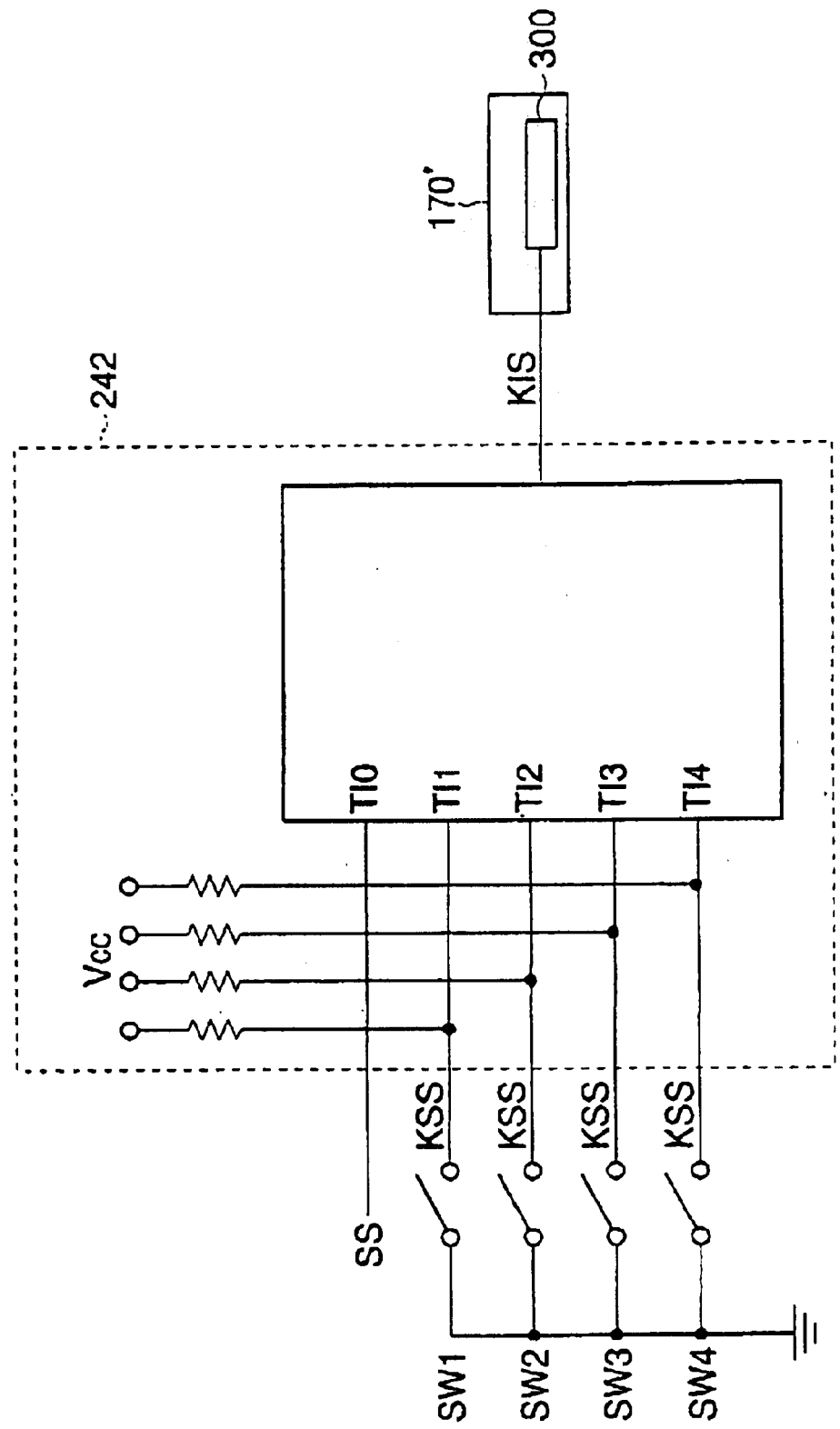
FIG. 15 is a block diagram of a video-processor detecting circuit.

FIG. 15 is a block diagram of the video-processor detecting circuit 242. FIG. 16 is a table T6 indicating the relationship between the indicating signal "KIS" and the signals input to the input TI0 to TI4.

The selecting signal "SS" fed from the selecting control circuit 223 shown in FIG. 12 and the video-processor setting signal "KSS" fed from the slide switches SW1, SW2, SW3, SW4 are input to inputs TI0, TI1, TI2, TI3, TI4 in the video-processor detecting circuit 242, respectively. In the video-processor detecting circuit 242, based on the selecting signal "SS" and the video-processor setting signal "KSS", the indicating signal "KIS" is output to the keyboard indicator 300 in the keyboard 170'. Note that, a keyboard memory (not shown) storing the indicating signal "KIS" is provided in the video-processor detecting circuit 242.

As shown in FIG. 15, A voltage Vcc is input to inputs TI1 to TI4, corresponding to the slide switches SW1, SW2, SW3, SW4 respectively, through resistors. When the slide switches SW1 to SW4 are all closed, "Low" level signals are input to TI1 to TI4 respectively. On the other hand, when the slide switches SW1 to SW4 are all open, "High" level signals are input to TI1 to TI4 respectively. As described above, the selecting signal "SS", input to TI0, is "High" when the first video-processor 40 is selected by the selector 200', and the selecting signal "SS" is "Low" when the second video-processor 60 is selected.

As shown in the table T6, the indicating signal "KIS" is set to one of 8 signals "E1 to E8" stored in the keyboard memory, and is determined in accordance with the level of the signals input to TI0 to TI4. For example, when the first video-processor 40 of the type-name "VPFC" and the second video-processor of the type-name "VPSC" are connected to the selector 200', the input signals at TI1, TI2, TI3, TI4 become "High", "Low", "High", "Low", respectively. Then, when the first video-processor 40 of the type-name "VPFC" is selected by the selector 200', the selecting signal "SS" becomes "High" and the indicating signal "KIS" is determined in accordance with the input signals at TI1, TI2. In this case, the indicating signal "KIS" is determined to be "E3". On the other hand, when the input signal TI0 is "Low" level, the second video-processor 60 of the type name "VPSC" is selected, the indicating signal "KIS" is determined to be "E7" as the input signals at TI3, TI4 are "High", "Low" respectively.

Figure 17:
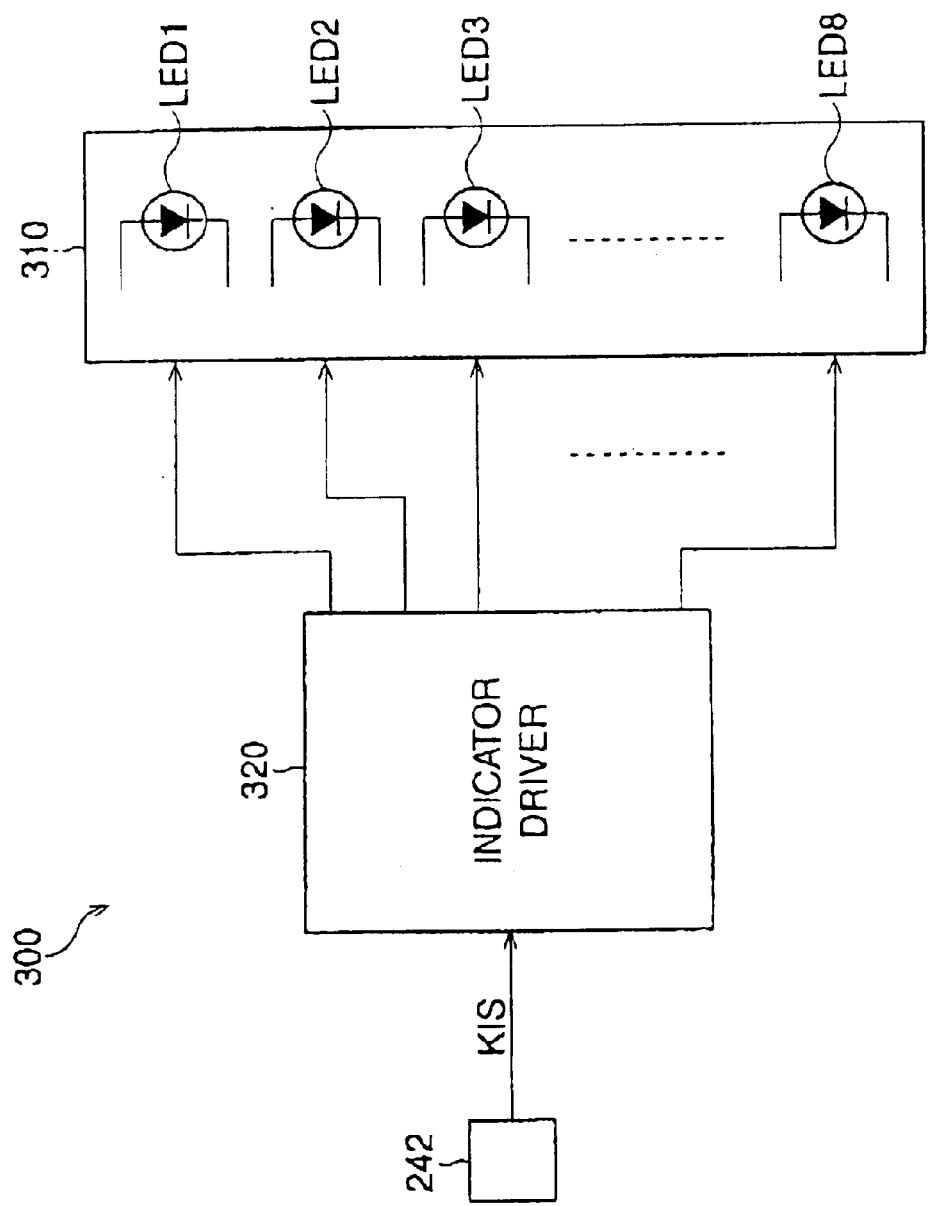
FIG. 17 is a block diagram of the indicating processor.

FIG. 17 is a block diagram of the keyboard indicator 300 and FIG. 18 is a table T7 indicating the relationship between the indicating signal "KIS" and illuminated LEDs.

The keyboard indicator 300 has a LED display 310 composed of 8 LEDs "LED1, LED2, . . . LED8" and an indicator driver 320 for driving the LED display 310. The LEDs "LED1", "LED2", "LED3", "LED4" correspond to the four types of video-processors using the R, G, B sequential method "VPFA", "VPFB", "VPFC", "VPFD" respectively. The LEDs "LED5", "LED6", "LED7", "LED8" correspond to the four types of video-processors using the color chip filter method "VPSA", "VPSB", "VPSC", "VPSD" respectively.

The indicator driver 320, in which the indicating signal "KIS" is input, drives one of the LEDs "LED1 to LED8" in the in accordance with the indicating signal "KIS", as shown in the table T7. For example, when the indicating signal "E3" is input to the indicating circuit driver 320, the LED "LED3" in the LED display 310 is illuminated.

Figure 19:
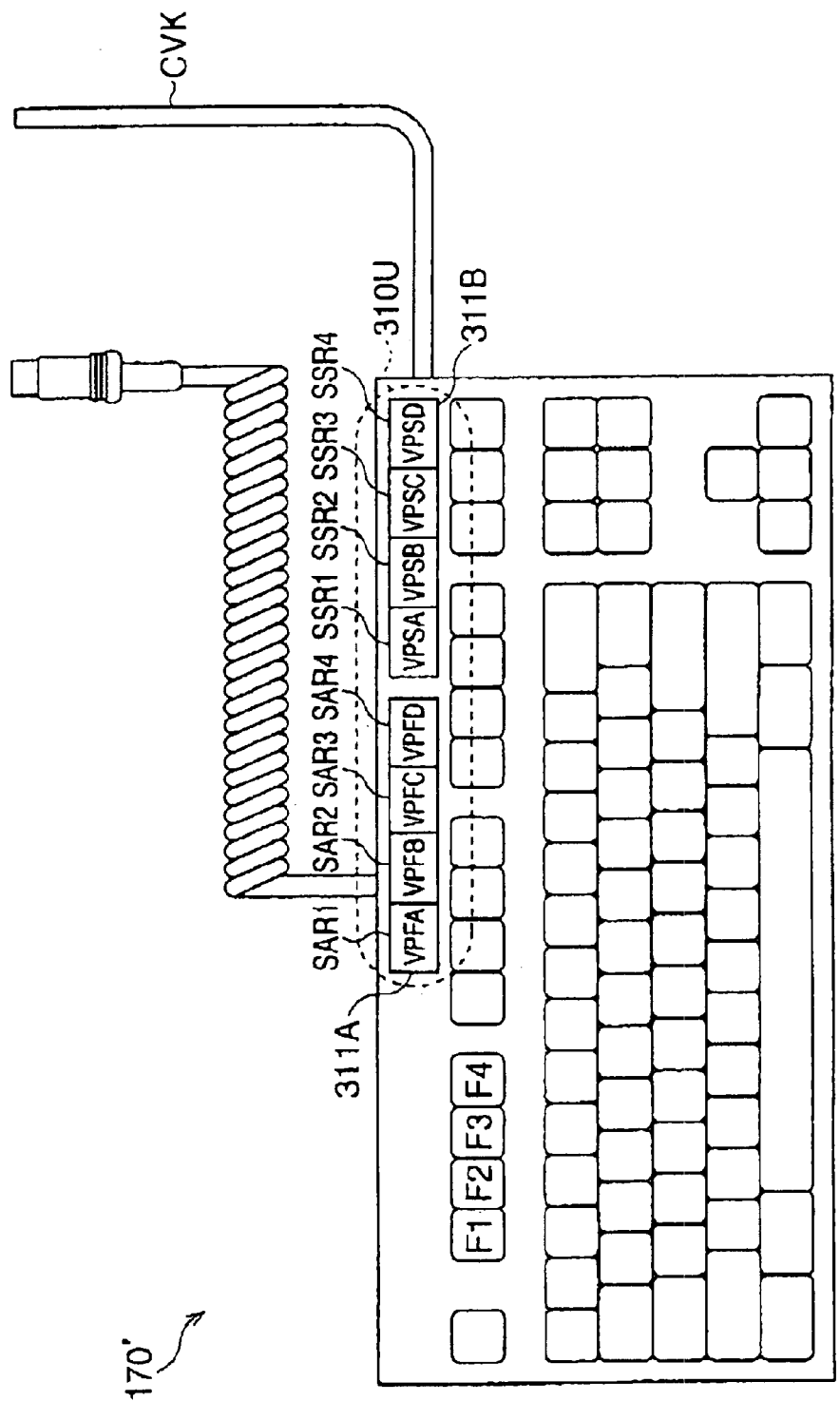
FIG. 19 is a plan view of a keyboard of the second embodiment.

FIG. 19 is a plan view of the keyboard 170'.

The indicating signal "KIS" is fed from the selector 200' to the keyboard 170' via the indicating circuit cable CVK, as described above. On the keyboard 170', an indicator panel 310U of the LED display 310 is formed, the indicator panel 310U is molded from a transparent material. The indicator panel 310U is divided into a first area 311A corresponding to the first video-processor 40 and a second area 311B corresponding to the second video-processor 60. On the first area 311A, the type-names of the four video-processors corresponding to the R, G, B sequential method "VPFA", "VPFB", "VPFC", "VPFD" are situated at the respective areas SAR1, SAR2, SAR3, SAR4. Similarly, on the second area 311B, the type-names of the four video-processors corresponding to the color chip filter method "VPSA", "VPSB", "VPSC", "VPSD" are situated at the respective areas SSR1, SSR2, SSR3, SSR4.

The position of the LEDs "LED1", "LED2", "LED3", "LED4" under the indicating circuit panel 310U correspond to the position of the type-name "VPFA", "VPFB", "VPFC", "VPFD" in the first area 311A, respectively. On the other hand, the position of the LEDs "LED5", "LED6", "LED7", "LED8" under the indicator panel 310U correspond to the position of the type-name "VPSA", "VPSB", "VPSC", "VPSD" in the second area 311B, respectively. For example, when the first video-processor 40 of the type-name "VPFC" is selected by the selector 200', "LED3" radiates light, thus the sign "VPFC" is illuminated.

The operation of a video-processor using a keyboard varies with the color photographing process and type of the video-processor. For example, in the case of the first video-processor 40 of the type-name "VPFC", corresponding to the R, G, B sequential method, the contour correction process to the object image is performed by operating the Function Key "F1", on the other hand, in the case of the second video-processor 60 of the type-name "VPSC", corresponding to the color chip filter method, the enlarging process of the object image is performed by operating the Function Key "F1". An operator recognizes that the first video-processor 40 of the type-name "VPFC" is selected by illuminating the sign "VPFC" and operates the keyboard 170' in accordance with the instructions for the first video-processor 40 of the type-name "VPFC".

In this way, in the second embodiment, the selected video-processor of the first and second video-processors 40, 60 is indicated by the keyboard indicator 300 provided at the keyboard 170'. Further, the type-name of the selected video-processor is shown on the indicator panel 310U.

Note that, other device, such as neon lamp, maybe provided on the keyboard 170' in place of the LEDs "LED1", "LED2", LED8".

Figure 20:
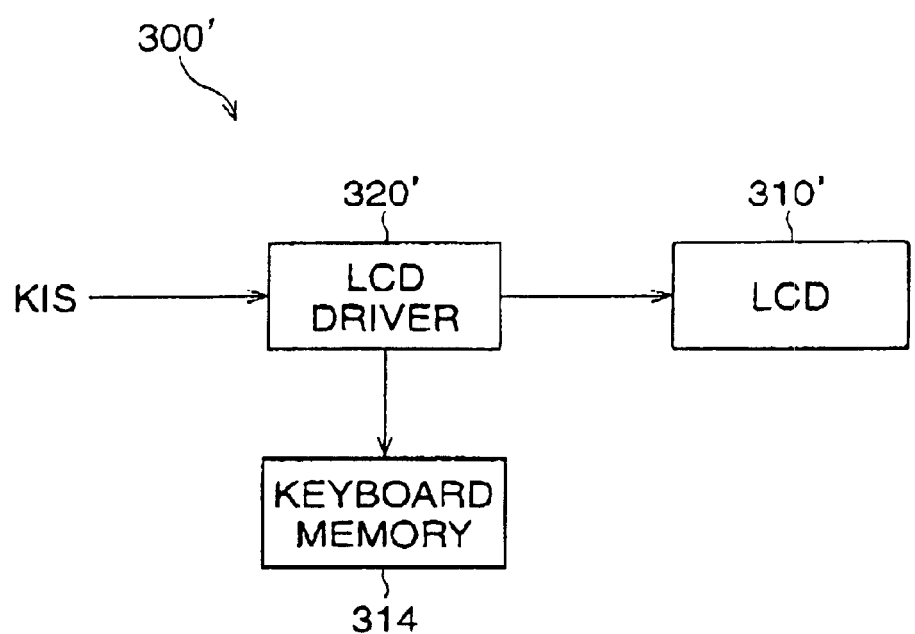
FIG. 20 is a block diagram of an indicating processor of a third embodiment.
Figure 21:
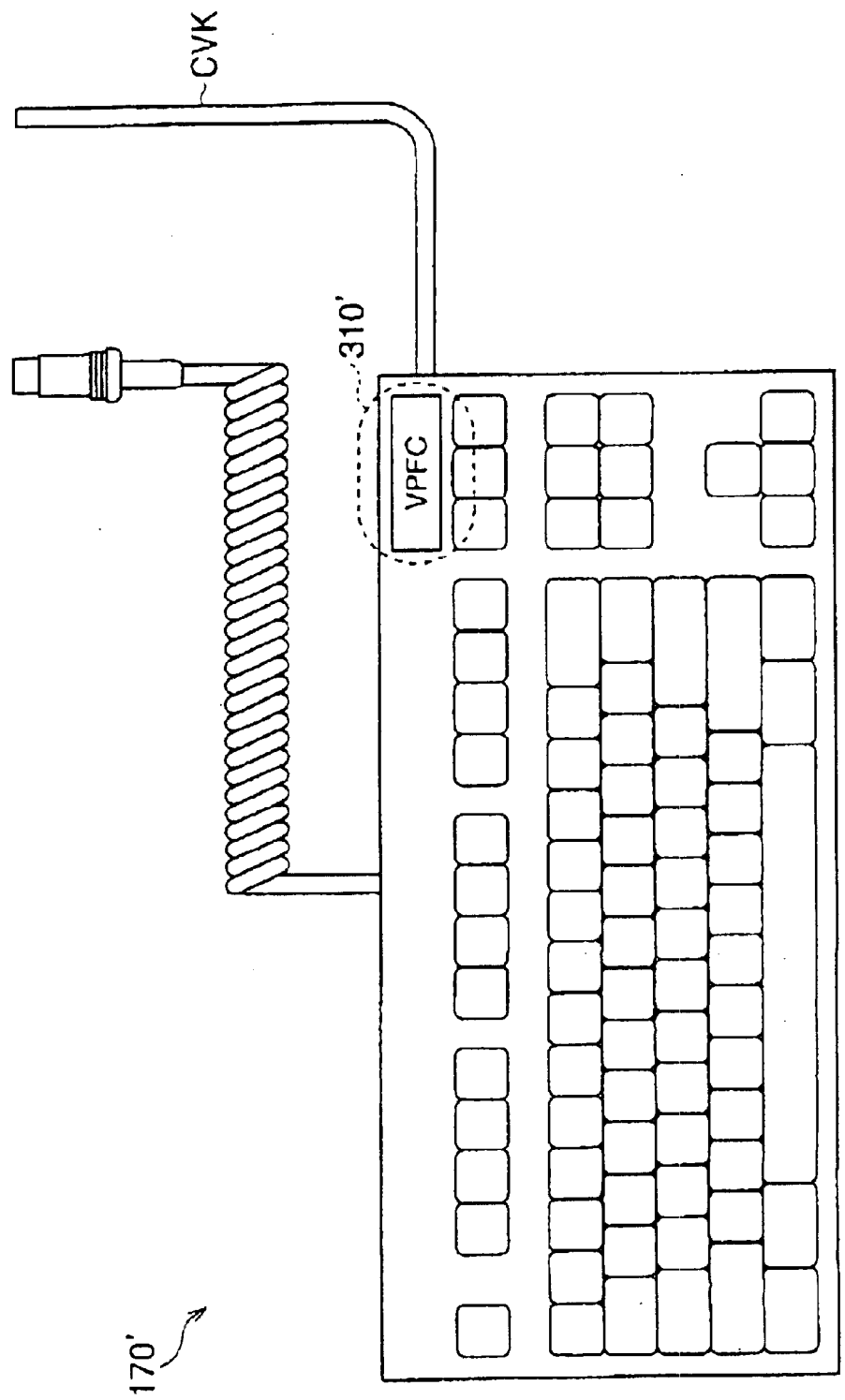
FIG. 21 is a plan view of a keyboard of the third embodiment.

With reference to FIGS. 20 and 21, the third embodiment is explained. The third embodiment is different from the second embodiment in that an LCD (Liquid Crystal Display) is applied. Since the reminder of this embodiment is similar to that of the second embodiment, designations remain the same.

FIG. 20 is a block diagram of a keyboard indicator 300'. The keyboard indicator 300' has a LCD panel 310', a LCD driver 320' and a keyboard memory 314. The LCD driver 320' for driving the LCD panel 310' accesses the keyboard memory 314 to read the type-name of the selected video-processor in accordance with the indicating signal "KIS".

The LCD 310' is then driven by the LCD driver 320' to display the type-name of the selected video-processor.

FIG. 21 is a plan view of the keyboard 170' of the third embodiment. The type-name of the selected video-processor, namely, one of "VPFA", "VPFB", "VPFC", "VPFD", "VPSA", "VPSB", "VPSC", "VPSD" is displayed on the LCD panel 310'. For example, when the first video-processor 40 of the type-name "VPFC" is selected, the type-name "VPFC" is displayed on the LCD panel 310', as shown in FIG. 21.

Note that, on the LCD panel 310', selected processor information, indicating which is of the first or second video-processors 40, 60 is selected, may be displayed with the processor type-name. For example, information "FIRST-VPFC (or SECOND-VPSC)" is displayed on the LCD panel 310'.

Figure 22:
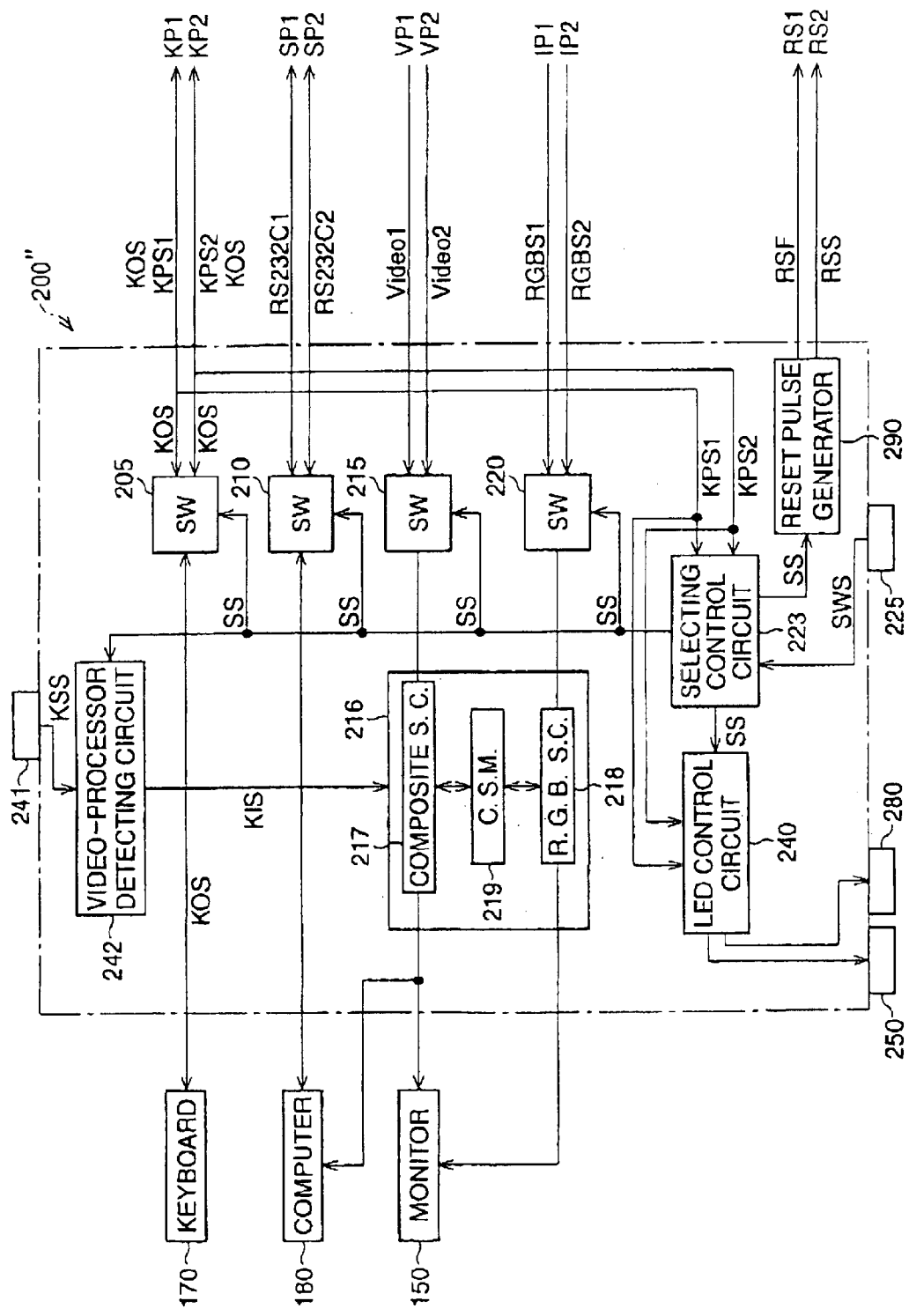
FIG. 22 is a block diagram of a selector of a fourth embodiment.
Figure 23:
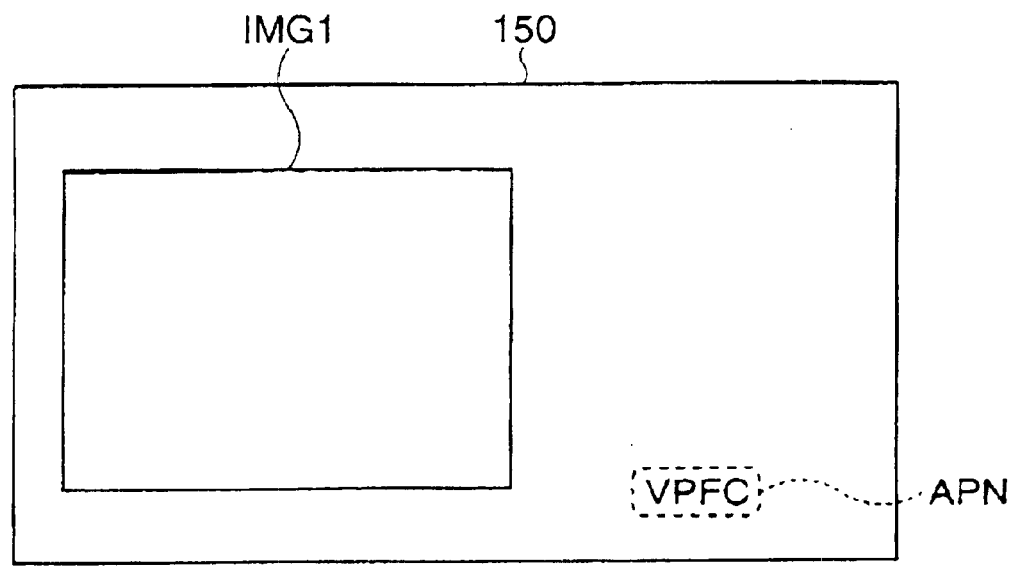
FIG. 23 is a view showing a screen of a monitor of the fourth embodiment.

With reference to FIGS. 22 and 23, the fourth embodiment is explained. The fourth embodiment is different from the second and third embodiments in that the type-name of the selected video-processor is displayed on the monitor. Since the reminder of this embodiment is similar to that of the second and third embodiments, designations remain the same.

FIG. 22 is a block diagram of a selector 200" of the fourth embodiment.

The selector 200" has a superimposing circuit 216 having a R, G, B superimposing circuit 218, a composite superimposing circuit 217 and a character signal memory 219. The selecting signal "SS" and the video-processor setting signal "KSS" are input to the video-processor detecting circuit 242. Then, indicating signal "KIS" is fed to the superimposing circuit 216 including the R, G, B superimposing circuit 218 and the composite superimposing circuit 217. Based on the indicating signal "KIS", the R, G, B superimposing circuit 218 and the composite superimposing circuit 217 accesses the character signal memory 219 to read character signal corresponding to the type-name of the selected video-processor. The character signal is then superimposed into the R, G, B component video signals "RGBS1" or "RGBS2" and the composite video signals "Video1" or "Video2" and by adjusting the timing of the superimposing so the type-name of the selected video-processor is displayed at a predetermined position on the monitor 150. Note that the adjustment of the superimposing is performed by a pulse generator (not shown).

FIG. 23 is a view showing a screen of the monitor 150. As shown in FIG. 23, the object image is displayed in the area IMG1 and character information, which is the type-name of the selected video-processor, is displayed in an are a APN a long side the object image. Here, the type-name "VPFC" is displayed. Similarly to, the third embodiment, to display the character information, for example, "FIRST-VPFC" or "SECOND-VPSC" in the area APN on the monitor 150, character signals corresponding to character information "FIRST" or "SECOND" may be superimposed into the composite and component video signals with the character signals corresponding to the type-name of the selected video-processor.

Note that, in the second, third and fourth embodiments, the LED control circuit 240 and the first and second indicator lamps 250, 280 (shown in FIGS. 12 and 22) may be left out of the selector 200' (200").

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Applications No. 11-322813 (filed on Nov. 12, 1999) and No. 2000-192258 (filed on Jun. 27, 2000), which are expressly incorporated herein, by reference, in their entireties.

What is claimed is:

1. An electronic endoscope system comprising:
a plurality of video-scopes, each having an image sensor on which an object image is formed;
a plurality of video-processors, to which said plurality of video-scopes are detachably connected respectively, that process image signals read from said corresponding image sensor to obtain and output video signals, respectively;
a selector, to which said plurality of video-processors are connected respectively, that selects one of said plurality of video-processors and outputs video signals fed from a selected video-processor of said plurality of video-processors;
a monitor, connected to said selector, that displays the object image on the basis of said video signals fed from said selector; and
an input device, connected to said plurality of video-processors via said selector, for operating said selected video-processor.

2. The electronic endoscope system of claim 1, wherein said selector detects an operating video-processor of said plurality of video-processors, which is turned ON and selectively outputs video signals fed from said operating video-processor to said monitor.

3. The electronic endoscope system of claim 1, wherein said selector detects a latest operating video-processor, which is turned ON last of said plurality of video-processors, and selectively outputs said video signals fed from said latest operating video-processor to said monitor, when at least two video-processors of said plurality of video-processors are turned ON.

4. The electronic endoscope system of claim 1, wherein a plurality of input device cables is connected between said plurality of video-processors and said selector respectively so as to transmit an input device operating signal, output from said input device, to said selected video-processor, said selector receiving a plurality of electric power signals, fed from said plurality of video-processors via said plurality of input device cables and representing an operating state of said plurality of video-processors, said selector detecting an operating video-processor, of said plurality of video-processors, which is turned ON when one of said plurality of video-processor is turned ON, and detecting a latest operating video-processor, which is turned ON last of said plurality of video-processors, when at least two video-processors of said plurality of video-processors are turned ON, in accordance with said plurality of electric power signals, said selector selectively outputting video signals, fed from one of said operating video-processor and said a latest operating video-processor, to said monitor.

5. The electronic endoscope system of claim 1, wherein said selector includes a manually operated selecting switch that selects one of said plurality of video-processors, said selector selectively outputs said video signals fed from said selected video-processor, which is selected by said selecting switch.

6. The electronic endoscope system of claim 1, wherein said selector includes a reset signal generator that feeds a reset signal to said selected video-processor of said plurality of video-processors, such that said selected video-processor is reset.

7. The electronic endoscope system of claim 1, wherein said plurality of video-processors is composed of a first video-processor and a second video-processor, said input device is a keyboard and said selector includes:
a video signal switch circuit, to which first video signals fed from said first video-processor and second video signals fed from said second video video-processor are input, that selectively outputs one of said first video signals and said second video signals to said monitor; and
a selecting controller that selects one of said first and second video-processors and controls said video signal switch circuit such that one of said first and second video signals, fed from said selected video-processor, are fed to said monitor.

8. The electronic endoscop system of claim 7, wherein said selector includes a keyboard switch circuit, to which a keyboard operating signal generated by operating said keyboard is input, that selectively feeds said keyboard operating signal to one of said first video-processor and said second video-processor, said selecting controller controlling said keyboard switch circuit such that said keyboard operating signal is fed to said selected video-processor.

9. The electronic endoscope system of claim 7, wherein a first electric power signal fed from said first video-processor and a second electric power signal fed from said second video-processor, which represent an operating state of said first and second video-processors respectively, are input to said selector, and said selecting controller detects which video-processor is turned ON of said first video-processor and said second video-processor, on the basis of said first and second electric power signals, and controls said video signal switch circuit such that one of said first video signals and said second video signals, output from one of said first and second video-processors, which is turned ON, is fed to said monitor.

10. The electronic endoscope system of claim 9, wherein said selecting controller detects which video-processor is turned ON last of said first video-processor and said second video-processor on the basis of said first and second electric power signals, when said first and second video-processors are turned ON, and controls said video signal switch circuit such that one of said first video signals and said second video signals, output from one of said first and second video-processors, which is turned ON last, is fed to said monitor.

11. The electronic endoscope system of claim 10, wherein a first and second keyboard cables are connected between said selector and said first and second video-processors respectively to transmit a keyboard operating signal generated by operating said keyboard to one of said first and second video-processors, said first and second electric power signals being fed to said selector via said first and second keyboard cables, respectively.

12. The electronic endoscope system of claim 10, wherein said selector includes a manually operated selecting switch for alternately selecting said first video-processor and said second video-processor, said selecting controller receiving an operating signal generated by operating said selecting switch and controlling said video signal switch circuit in accordance with said operating signal such that one of said first and second video signals, fed from one of said first and second video-processors, which is selected by said selecting switch, is fed to said monitor.

13. The electronic endoscope system of claim 12, wherein said selecting controller includes:
a JK flip-flop with clock, clear and preset inputs, to which said first electric power signal and said second electric power signal are input to said clear and preset inputs respectively and said operating signal is input to said clock input, that outputs a state signal in accordance with levels of said first and second electric power signals and an input of said operating signal;

an inverter that inverts a level of said second electric power signal to generate an inverted second electric power signal; and a multiplexer, to which said state signal, said first electric power signal and said inverted second electric power signal are input, that selectively outputs one of said first electric power signal and said inverted second electric power signal to said video signal switch circuit as a selecting signal, in accordance with a level of said state signal, said video signal switch circuit being switched in accordance with a level of said selecting signal.

14. The electronic endoscope system of claim 13, wherein said selector includes a reset signal generator that feeds a reset signal to said selected video-processor of said first and second video-processors such that said selected video-processor is reset, when a level of said selecting signal changes.

15. The electronic endoscope system of claim 1, further comprising a computer connected to said selector, to which a memory device for storing the object image and a display for said computer are connected, wherein said selector selectively outputs said video signals fed from said selected video-processor to said computer.

16. A selector incorporated in an electronic endoscope system including a plurality of video-processors and a monitor, said selector comprising:

a video signal switch circuit, to which a plurality of video signals fed from said plurality of video-processors respectively are input, that selectively outputs one of said plurality of video signals to said monitor; and a selecting controller that selects one of said plurality of video-processors and controls said video signal switch circuit such that video signals from a selected video-processor are fed to said monitor.

17. The selector of claim 16, wherein an input device for operating said selected video-processor, included in said electronic endoscope system, is connected to said selector and said selector includes an input device signal switch circuit, to which an input device operating signal generated by operating said input device is input, that selectively feeds said input device operating signal to one of said plurality of video-processors, said selecting controller controlling said input device signal switch circuit such that said input device operating signal is fed to said selected video-processor.

18. An electronic endoscope system comprising:

a plurality of video-scopes, each having an image sensor on which an object image is formed;

a plurality of video-processors, to which said plurality of video-scopes are detachably connected respectively, that process image signals read from said corresponding image sensor to obtain and output video signals, respectively;

a selector, to which said plurality of video-processors are connected respectively, that selects one of said plurality of video-processors and outputs video signals from a selected video-processor of said plurality of video-processors;

a monitor, connected to said selector, that displays the object image on the basis of said video signals fed from said selector;

an input device, connected to said plurality of video-processors via said selector, for operating said selected video-processor; and an indicator that visually indicates said selected video-processor of said plurality of video-processors.

19. The electronic endoscope system of claim 18, wherein said indicator is provided at said selector, such that said selected video-processor is indicated on said selector.

20. The electronic endoscope system of claim 19, wherein said indicator includes indicating lamps, a number of which corresponds to the number of said video-processors, said indicator illuminating one lamp, corresponding to said selected video-processor, of said indicating lamps.

21. The electronic endoscope system of claim 18, wherein said indicator displays processor information representing said selected video-processor on said monitor.

22. The electronic endoscope system of claim 21, wherein said indicator has a superimposing circuit that superimposes a character signal representing said selected video-processor into said video signals fed from said selected video-processor, such that said processor information is displayed at a predetermined position on said monitor.

23. The electronic endoscope system of claim 18, wherein said input device is a keyboard and said indicator includes:

a selected processor displayer that displays said selected video-processor, said selected processor displayer being provided at said keyboard; and a processor detector, provided in said selector, that detects said selected video-processor and feeds an indicating signal corresponding to said selected video-processor to said selected processor displayer, said indicator indicating said selected video-processor at said selected processor displayer in accordance with said indicating signal.

24. The electronic endoscope system of claim 23, wherein said selected processor displayer includes a plurality of luminance devices, a number of which corresponds to the number of said video-processors, said indicator illuminating one luminance device corresponding to said selected video-processor, of said plurality of luminance devices.

25. The electronic endoscope system of claim 23, wherein said selected processor displayer includes an LCD (Liquid Crystal Device), said indicator displaying said selected video-processor on said LCD.

26. The electronic endoscope system of claim 18, wherein said input device is a keyboard and said selector includes a processor type setting switch for registering types of said plurality of video-processors, said indicator indicating a type of said selected video-processor in accordance with a setting of said processor type setting switch.

27. The electronic endoscope system of claim 26, wherein said plurality of said video-processors is composed of a first video-processor corresponding to a R, G, B sequential method for a color photographing process and a second video-processor corresponding to a color chip filter method for the color photographing process, said indicator indicating a type of one of said first video-processor and said second video-processor.

28. A selector incorporated in an electronic endoscope system including a plurality of video-processors, an input device and a monitor, said selector comprising:

a video signal switch circuit, to which a plurality of video signals fed from said plurality of video-processors respectively are input, that selectively outputs one of said plurality of video signals to said monitor;

a selecting controller that selects one of said plurality of video-processors and controls said video signal switch circuit such that video signals from a selected video-processor are fed to said monitor;

an input device signal switch circuit, to which an input device operating signal generated by operating said input device is input, that selectively feeds said input device operating signal to one of said plurality of video-processors, said selecting controller controlling said input device signal switch circuit such that said input device operating signal is fed to said selected video-processor; and an indicating processor that superimposes a character signal representing said selected video-processor into said video signals so as to display said selected video-processor on said monitor.

29. A selector and an input device incorporated in an electronic endoscope system including a monitor and a plurality of video-processors, said selector and input device comprising:

a video signal switch circuit, provided in said selector, to which a plurality of video signals fed from said plurality of video-processors respectively are input, that selectively outputs one of said plurality of video signals to said monitor;

a selecting controller, provided in said selector, that selects one of said plurality of video-processors and controls said video signal switch circuit such that video signals output from a selected video-processor are fed to said monitor;

an input device signal switch circuit, provided in said selector, to which an input device operating signal generated by operating said input device is input, that selectively feeds said input device operating signal to one of said plurality of video-processors, said selecting controller controlling said input device signal switch circuit such that said input device operating signal is fed to said selected video-processor;

an input device indicator, provided at said input device, that has a selected processor displayer for displaying said selected video-processor; and a processor detector, provided in said selector, that detects said selected video-processor and feeds an indicating signal corresponding to said selected video-processor to said input device indicator, said input device indicator displaying said selected video-processor at said selected processor displayer in accordance with said indicating signal.

30. A selector incorporated in an electronic endoscope system including a plurality of video-processors, an input device and a monitor, said selector comprising:

a video signal switch circuit, to which a plurality of video signals fed from said plurality of video-processors respectively are input, that selectively outputs one of said plurality of video signals to said monitor;

a selecting controller that selects one of said plurality of video-processors and controls said video signal switch circuit such that video signals from a selected video-processor are fed to said monitor;

an input device signal switch circuit, to which an input device operating signal generated by operating said input device is input, that selectively feeds said input device operating signal to one of said plurality of video-processors, said selecting controller controlling said input device signal switch circuit such that said input device operating signal is fed to said selected video-processor; and an indicator that visually indicates said selected video-processor of said plurality of video-processors on said selector.

* * * * *